US006334446B1

(12) United States Patent
Beyar

(10) Patent No.: US 6,334,446 B1
(45) Date of Patent: Jan. 1, 2002

(54) MEDICAL SLING PROCEDURES AND ANCHOR INSERTION METHODS AND DEVICES

(75) Inventor: Mordechay Beyar, Caesarea (IL)

(73) Assignee: American Medical Systems, Inc., Minnetonka, MN (US)

( * ) Notice: Subject to any disclaimer, the term of this patent is extended or adjusted under 35 U.S.C. 154(b) by 0 days.

(21) Appl. No.: 09/287,867

(22) Filed: Apr. 7, 1999

Related U.S. Application Data

(60) Continuation of application No. 08/733,798, filed on Oct. 18, 1996, now Pat. No. 5,972,000, which is a continuation-in-part of application No. 08/622,598, filed on Mar. 26, 1996, now Pat. No. 5,807,406, which is a division of application No. 08/150,517, filed on Nov. 10, 1993, now Pat. No. 5,520,700.
(60) Provisional application No. 60/012,205, filed on Feb. 23, 1996, and provisional application No. 60/005,348, filed on Oct. 18, 1995.

(30) Foreign Application Priority Data

Nov. 13, 1992 (IL) ............................................. 103737
Jan. 8, 1999 (IL) ............................................. 127978

(51) Int. Cl.⁷ ........................... A61B 17/04; A61B 19/00
(52) U.S. Cl. ...................... 128/898; 606/139; 606/73; 606/75; 606/232; 600/37
(58) Field of Search .......................... 128/898; 600/37; 606/139, 73, 75, 232

(56) References Cited

U.S. PATENT DOCUMENTS 2,738,790 A   3/1956   Todt et al.
3,995,619 A   12/1976  Glatzer (List continued on next page.)

FOREIGN PATENT DOCUMENTS

DE   2 305 815      2/1973
RU   1225547        4/1986
WO   WO 93/19678   10/1993
WO   WO 98/19606    5/1998

OTHER PUBLICATIONS

McGuire E..J.., Abdominal Procedure for Stress Incontinence, *Urol. Clin. North Am.*, 12(2): 285–90 (May 1985).
Blaivas J. G., Jacobs B. Z., Pubovaginal Fascial Sling for the Treatment of Complecated Stress Urinary Incontinence, *J. Urol.* 145(6): 1214–18 (Jun. 1991).
McGuire, E.J., Lytton, B., Pubovaginal Sling Procedure for Stress Incontinence, *J. Urol.* 119(1): 82–4 (Jan. 1978).
Peripubic Urethropexy for Urinary Stress Incontinence in Women by Chester C. Winter, MD, Urology, Oct. 1982, vol. XX, No. 4, p. 408–411.
Bone Fixation Technique for Transvaginal Needle Suspension by Gary E. Leach, MD; Urology, May 1988, vol. XXXI, No. 5, pp. 388–390.
The Sling Procedure for Urinary Stress Incontinence, by Edward J. McGuire, MD; Profiles in Urology, pp. 3–18.
Sling (advertisement) Microvasive Boston Scientific Corporation.
Review of an 8–Year Experience with Modifications of Endoscopic Suspension of the Bladder Neck for Female Stress Incontinence by Kevin R. Loughlin, Willet F. Whitmore, III, Reuben F. Gittes and Jerome P. Richie, The Journal of Urology, vol. 143, Jan. 1990, p. 44–5.

(List continued on next page.)

*Primary Examiner*—Michael J. Milano
*Assistant Examiner*—Choon P. Koh
(74) *Attorney, Agent, or Firm*—James W. Inskeep; Oppenheimer Wolff & Donnelly LLP

(57) ABSTRACT

A procedure for treating urinary stress incontinence by using bone anchors, whether screw or staple type, with or without suture, inserted pervaginally for use with a sling material for supporting the bladder neck and/or proximal uretha.

23 Claims, 30 Drawing Sheets

U.S. PATENT DOCUMENTS

| | | | |
|---|---|---|---|
| 4,172,458 A | | 10/1979 | Pereyra |
| 5,013,292 A | | 5/1991 | Lemay |
| 5,085,661 A | | 2/1992 | Moss |
| 5,188,636 A | | 2/1993 | Fedotov |
| 5,281,237 A | | 1/1994 | Gimpelson |
| 5,328,077 A | * | 7/1994 | Lou .......................... 227/175 |
| 5,413,598 A | * | 5/1995 | Moreland ................ 623/1.49 |
| 5,439,467 A | | 8/1995 | Benderev et al. |
| 5,520,700 A | | 5/1996 | Beyar et al. |
| 5,544,664 A | | 8/1996 | Benderev et al. |
| 5,571,139 A | * | 11/1996 | Jenkins, Jr. ................ 606/232 |
| 5,611,515 A | | 3/1997 | Benderev et al. |
| 5,633,286 A | * | 5/1997 | Chen .......................... 524/474 |
| 5,683,349 A | * | 11/1997 | Makower et al. ........... 600/214 |
| 5,807,403 A | | 9/1998 | Beyar et al. |
| 5,836,314 A | | 11/1998 | Benderev et al. |
| 5,944,732 A | * | 8/1999 | Raulerson et al. .......... 606/167 |
| 6,053,935 A | * | 4/2000 | Brenneman et al. ........ 606/232 |

OTHER PUBLICATIONS

Experience with a Simplified Technique for the Treatment of Female Stress Urinary Incontinence by R.O. Parra and L. Shaker, British Journal of Urology (1990), p. 615–7.

A Comparision of Endoscopic Suspension of the Vesical Neck with Suprapubic Vesicourethropexy for Treatment of Stress Urinary Incontinence by Julia R. Spencer, Vincent J. O'Conor, Jr. and Anthony J. Schaeffer, The Journal of Urology, vol. 137, Mar. 1987.

Marshall–Marchetti Procedure Modification by Charles F. McKiel, Jr. Edwin C. Graf and Daniel H. Callahan, The Journal of Urology, vol. 96, Nov. 1966, p. 737–9.

Endoscopic Suspension of the Vesical Neck for Urinary Incontinence by Thomas A. Stamey, MD; Surgery, Gynecology & Obsterics, Apr. 1973, vol. 136, p. 547–54.

Modified Bladder Neck Suspension for Female Stress Incontinence by Shlomo Raz, MD, Urology, Jan. 1981, vol. XVII, No. 1, p. 82–5.

Female Urinary Incontinence by George D. Webster; Urologic Surgery, pp. 665–679.

No–Incision Pubovaginal Suspension for Stress Incontinence by Ruben F. Gittes and Kevin R. Loughlin, The Journal for Urology, vol. 138, Sep. 1987.

Therapy of Urinary Stress Incontinence in Women Using Mitek GII Anchors by Valenzio C. Mascio, MD, Mitek brochure.

Anchor Fixation and Other Modifications of Endoscopic Bladder Neck Suspension by Theodore V. Benderev, MD, Urology, Nov. 1992, vol. 40, No. 5, 409–18.

* cited by examiner

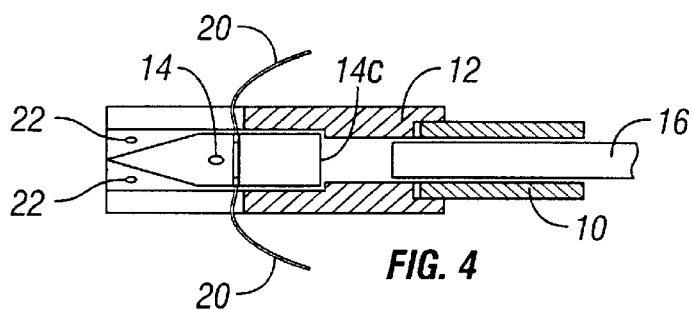
FIG. 4
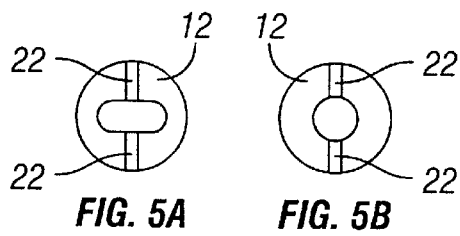
FIG. 5A  FIG. 5B
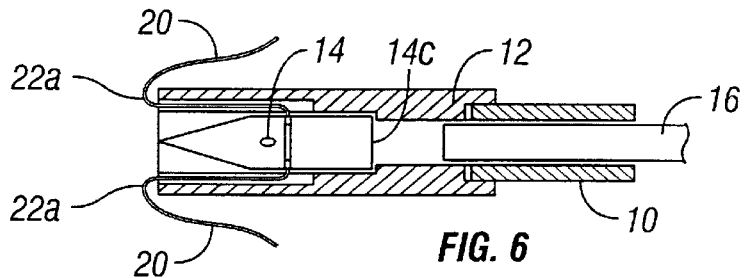
FIG. 6
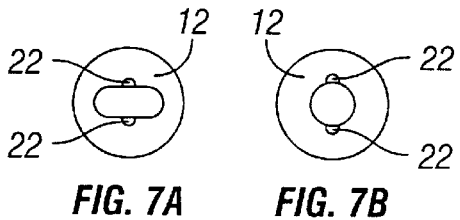
FIG. 7A  FIG. 7B
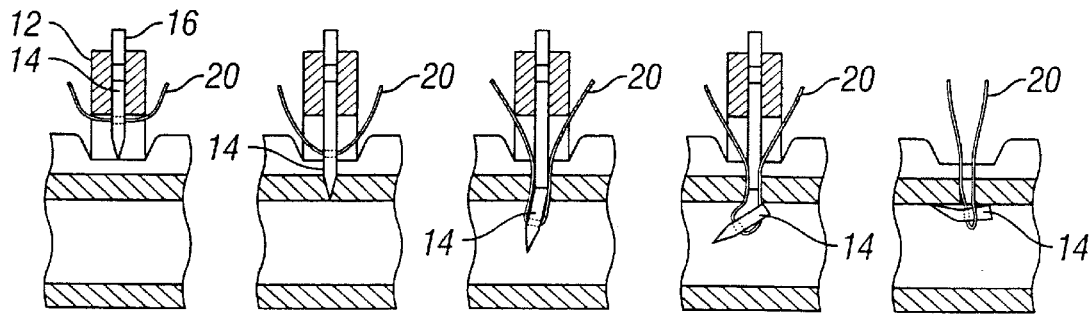
FIG. 8A  FIG. 8B  FIG. 8C  FIG. 8D  FIG. 8E

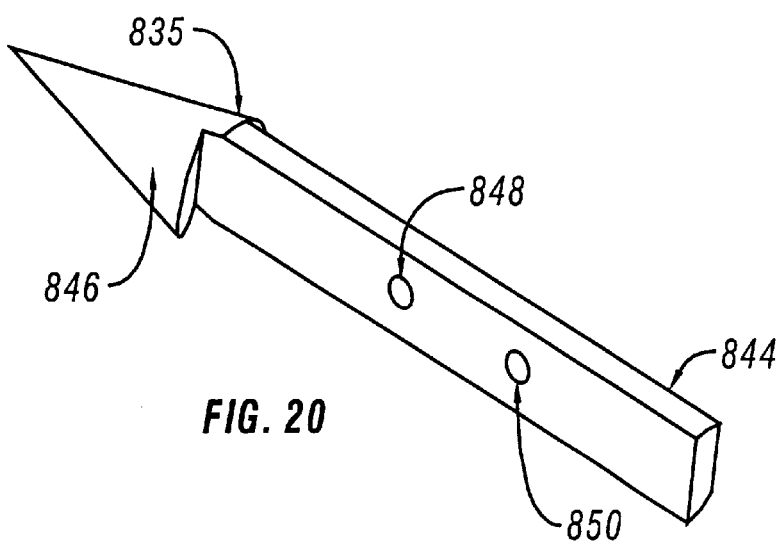
FIG. 20
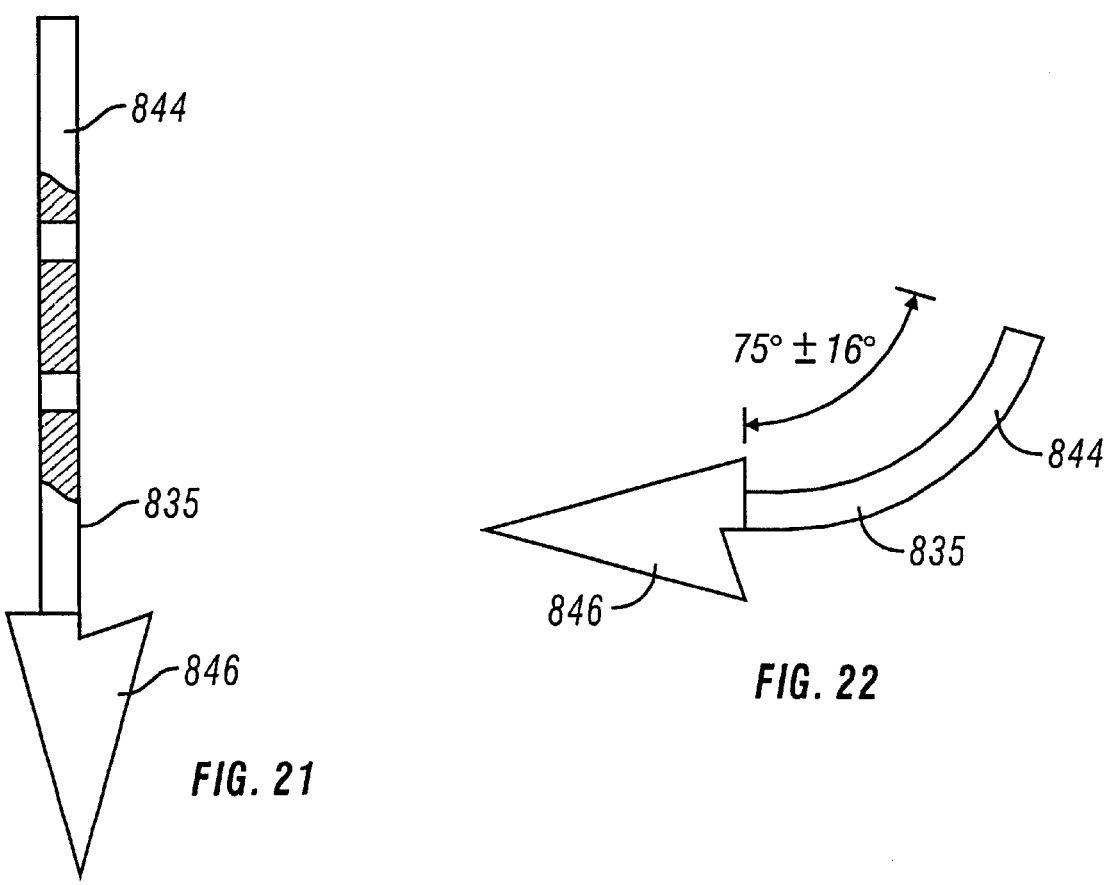
FIG. 21
FIG. 22

MEDICAL SLING PROCEDURES AND ANCHOR INSERTION METHODS AND DEVICES

RELATED APPLICATIONS

The present application is a Continuation of U.S. patent application Ser. No. 08/733,798 filed Oct. 18, 1996 (now U.S. Pat. No. 5,972,000); which is a Continuation-In-Part of U.S. patent application Ser. No. 08/622,598, filed Mar. 26, 1996 (now U.S. Pat. No. 5,807,406); which is a Divisional of U.S. patent application Ser. No. 08/150,517, filed Nov. 10, 1993 (now U.S. Pat. No. 5,520,700); which claims priority of Israeli Patent Application No. 10373, filed Nov. 13, 1992 and issued May 19, 1997. This application incorporates U.S. Provisional Application No. 60/012,205, filed Feb. 23, 1996, U.S. Provisional Patent Application No. 60/005,348, filed Oct. 18, 1995, and Israel Patent Application No. 127978, filed Jan. 8, 1999, in their entirety, by this reference.

FIELD OF THE INVENTION

The present invention relates to pervaginal sling procedures using bone anchors.

BACKGROUND OF THE INVENTION AND DESCRIPTION OF THE PRIOR ART

Urinary stress incontinence, i.e., the inability to control urination from the bladder, is a distressing problem for more than ten percent of elderly women as well as for many young women. Different theories exist to explain the pathology. In a normally anatomically positioned bladder, the proximal urethra and the bladder are in pressure continuity with the abdominal cavity, so that an increase in abdominal pressure is transmitted both to the bladder and to the proximal urethra, resulting in normal continence. However, particularly among elderly women, the bladder and the proximal urethra tend to descend from their normal or original anatomic positions such that the bladder neck and proximal urethra move away from the posterior wall of the pubic bone. When this occurs, the proximal urethra is no longer in pressure continuity with the abdominal cavity; therefore, an unintended increase in intra-abdominal pressure (e.g. by laughing or coughing) results in an increase in intravesical pressure, but no change in the urethral closing pressure, thereby producing so-called stress incontinence. It also appears that as the bladder descends, the urethra becomes shorter and curved, so that its radial tonic muscle contraction is reduced, contributing to incontinence. Another pathology may arise from urethral sphincteric damage (type III incontinence).

Most of the surgical treatments for stress incontinence involve bladder neck suspension. One treatment is by an open surgical operation, involving an incision in the abdominal wall and/or anterior vaginal wall, to reposition and suspend the bladder and proximal urethra to their normal or original anatomic positions. This is done by suspension of the bladder neck and periurethral tissue to the posterior wall of the pubic bone. In another surgical procedure, the bladder neck is elevated by suspension of suture threads passing, with the aid of long needles, from both sides of the urethra and the bladder neck to the lower abdominal fascia or superior pubic bone ramus.

In prior U.S. patents and applications (e.g., the Related Applications referenced above, including U.S. Pat. No. 5,520,700, issued May 28, 1996, pending U.S. patent application Ser. No. 08/733,798, filed Oct. 18, 1996, and pending Israeli Patent Application Serial No. 127978, filed Jan. 8, 1999 and entitled "Incontinence Device", the disclosures of which are hereby incorporated by reference), apparatus and methods are disclosed which allow treatment of urinary stress incontinence by a pervaginal procedure. As disclosed therein, an inserter device can be utilized for ejecting and implanting a bone anchor (e.g. a staple or a bone screw) through the vaginal tissue to enter the pubic bone. Further, a non-linear inserter device can be used to install a bone anchor by either injecting (in the case of a staple) or screwing the bone screw into the pubic bone, with or without vaginal incision. The suture thread that is secured to the bone anchor(s) (e.g staple(s) or bone screw(s)), can be used to suspend the bladder neck and the periurethral tissue to the posterior wall of the pubic bone. In addition, the suture thread can be used to perform a sling procedure in which a piece of material, such as abdominal fascia, fascia lata, cadaveric fascia or synthetic material, is positioned below the bladder neck and attached at both extremities to the pubic bone, by the threads. (In the classic sling operation, the sling material is attached to the abdominal fascia either directly or by means of threads).

It has been found, however, in stapler devices, and especially those that require high impact for bone implantation, that the ejection of the staple from the device causes the stapler to recoil. As is apparent from basic physics, the action of ejecting the staple from the stapler is associated with a reaction force which forces the inserter/stapler and the hand of the individual (the physician) implanting the same to move backwards. As a result, the physician must take this recoil into account and use force to firmly press the stapler against the pubic bone to ensure that the bone anchor is properly and effectively ejected and implanted. Anyone familiar with carpentry-type staple guns is familiar with this recoil. If pressure is not placed over the head end of the stapler, and the surface into which the staple is driven is hard (as in the case of bone), the staple will not be fully implanted, but, rather, the user's hand will recoil. The medical stapler should also be held perpendicular to the bone surface. The stapler must be held in that position with the stapler held firmly during and through the ejection process so that the stapler does not shift its position as a result of the recoil. Otherwise, undue movement of the stapler because of recoil can result in a staple being ejected in an incorrect orientation, or incompletely ejected into the bone of the patient. This problem is especially apparent where the material into which the staple is ejected is bone and the physical confines of the space where the medical physician's hands are working is limited, i.e., within a vagina.

Similarly, where the inserter is a screwdriver type and the anchor is a screw type anchor, unless a hole is pre-drilled in the insertion site, constant firm pressure must be applied through the axis of the anchor (perpendicular to the pubic bone) to assist the self-tapping property of the anchor to facilitate insertion during screwing. The medical screwdriver type inserter must, therefore, be held in the correct position relative to the patient's anatomy through the insertion process.

A purpose of the present invention is to provide mechanical leverage, which facilitates a constant pressure at the insertion site to minimize the effect of this recoil, increasing the ease of use of an inserter device in a medical procedure (whether a pusher or impact type inserter, or a screw inserter), and increasing an inserter device's effectiveness. This furthers the self-tapping property of the bone anchor, whether it be an impact type or screw type anchor. A screw type inserter device can be used for greater ease and effectiveness of use over an impact type device, particularly in a pervaginal medical procedure.

A further purpose of the present invention is to provide leverage in the per vaginal insertion of a bone anchor into the pubic bone. The present invention allows the physician to employ a pulling force perpendicularly against the pubic bone of the patient, and to conveniently do so with one hand. The leverage, degree of accuracy and ease of insertion are believed to be significantly enhanced by the present invention.

In one embodiment, the present invention relates to per vaginal bone screw or staple insertion, without first drilling a hole in the bone, by use of a non-linear or C-shaped inserter having a rotating intravaginal head for per vaginal injecting or screwing with or without vaginal wall incision. An additional purpose of the present invention is to provide a screw or staple type bone anchor and related device and procedures for per vaginal incisionless or minimal incision bladder neck suspension.

In a further embodiment, the invention relates to medical sling procedures. It is believed by some physicians that a sling procedure has better long term results of bladder neck suspension for type I, II, and III incontinence. Therefore, the invention relates, in a further embodiment, to medical sling procedures using bone anchors, either staples or screws, with or without suture, and preferably further using a non-linear anchor inserter.

Such sling procedures (or "sling operations") are medical procedures in which a sling material is positioned below the bladder neck and/or the urethra to give support like a hammock. Sling procedures have been described in the art in such references as: Blavias J. G., Jacobs B. Z., *Pubovaginal fascial sling for the treatment of complicated stress urinary, incontinence, J. Urol.* 145(6):1214–8 (June 1991); McGuire E. J., Lytton B, *Pubovaginal sling procedure for stress incontinence, J. Urol.* 119(1): 82–4 (Jan. 1978); and, McGuire E. J., *Abdominal procedure for stress incontinence, Urol. Clin. North Am.,* 12(2):285–90 (May 1985); the disclosures of which are incorporated herein by reference.

In these relatively minimally invasive techniques (which have recently become more common), the bladder neck and/or urethra is supported by a sling, so that the urethra is partially compressed and/or has a support below it. Thus, during straining and/or bladder/uretheral descent, pressure is applied between the urethra and the sling, thereby closing its lumen.

Benderev et. al, in U.S. Pat. No. 5,836,314 and Brenneman et al, in PCT publication WO 98/19606, the disclosures of which is incorporated herein by reference, describe examples of procedures for treating incontinence. Two or more bone anchors are attached to the pubic bone, and each anchor is pre-threaded with a suture. Brenneman suggests that a sling be attached to the sutures and that the the sutures then be pulled tight and knotted, thereby urging the sling towards the pubic bone. Benderev suggests integrally molding one end of a suture with a "suture support", which suture support is provided to prevent damage to the urethra by the sutures.

SUMMARY OF THE INVENTION

An object of the present invention is to provide a stapler device which is particularly useful for fastening threaded staples to a bone for various medical purposes, particularly to treat urinary stress incontinence.

According to one embodiment of the present invention, there is provided a stapler device comprising: a handle manually grippable by a user, containing a drive mechanism and a trigger to activate the drive mechanism; a barrel fixed to the handle; a guide for holding a staple to be ejected; and an ejector driven by the drive, mechanism, movable in the barrel for ejecting a staple out through an end of the guide; characterized in that the end of the guide is formed to accommodate a suture thread fixed to the staple.

In one described embodiment, the barrel is rigid for holding the guide in a fixed prescribed direction; and in a second described embodiment, it is flexible to allow pointing of the guide in a desired direction.

In a third described embodiment, the end of the guide is formed with a slot, or a pair of slots, for receiving the thread fixed to the staple; and in a fourth described embodiment, it is formed with a recess, or a pair of recesses, for receiving the thread fixed to the staple.

Such an anchoring device is particularly useful for treating women suffering from urinary stress incontinence caused by the descending of the bladder and the proximal urethra from their normal anatomical positions. Thus, the anchor may be ejected through the vaginal wall to enter the pubic bone, and the suture thread secured to the anchor may be used for attaching the bladder neck and the proximal urethra to the posterior wall of the pubic bone. Such an anchor device may also be used in other applications; for example, in medical operations for the fixation of a shoulder capsule in a person suffering from chronic shoulder dislocation.

The present invention also addresses the difficulties experienced in the prior art by providing a "C", "V" or other non-linear shaped insertion device for use in medical applications, and especially, per vaginal insertions of anchors of any type into the pubic bone of a patient. The insertion device, which may be rigid or flexible, is positioned during use so that force may be applied through the axis of the anchor. The weight of a patient can contribute to the force applied by the physician to firmly press the device against the patient's anatomy, so as to minimize the effects of the problems normally associated with recoil. The present device is directed both toward a stapler device for use to eject a staple type bone anchor, and toward a screw type bone anchor inserter. The inserters can be useful in other applications, as well, beyond those applications disclosed herein.

Accordingly, it is an object of the present invention to provide an insertion device which minimizes recoil during ejection of a bone anchor into bone.

It is further an object of the present invention to provide an insertion device which minimizes recoil during per vaginal insertion of a bone anchor into the pubic bone and otherwise allows constant pressure to be applied during the per vaginal insertion of self-tapping anchors into the pubic bone.

It is a further object of the present invention to provide a device which facilitates additional pressure to be applied to the insertion site beyond the direct pushing pressure applied by the physician in the case of a linear inserter held in place in the vagina by the physician's hand. With the present non-linear inserter, the physician's hand is used to pull the inserter against the resistive force of the pubic bone, thereby forcing the anchor tip to penetrate the bone cortex. It is far easier to insert a bone anchor, staple or screw with the hands external to the vagina and by use of the pulling force perpendicular to the bone surface.

It is further an object of the present invention to provide an inserter device for medical applications which improves the accuracy, effectiveness and ease of anchor insertions.

It is further an object of the present invention to utilize the physical pulling force on the inserter to further fixate the anchor tip penetration force perpendicular to the bone surface and in line with the physician pulling force.

It is further an object of the present invention to utilize at least a portion of the weight of a patient's body to maintain a bone anchor or screw inserter in firm contact with the patient during insertion of a bone anchor or screw into the patient's bone.

It is a further object of the present invention to use at least a portion of the weight of a patient as counter balancing leverage against the recoil of a bone anchor/staple/screw being inserted into the bone of a patient.

It is further an object of the present invention to provide improved procedures and inserter devices for inserting bone anchors, staples and/or screws in medical procedures.

It is further an object of the present invention to provide an improved bone anchor inserter for use in and to facilitate medical applications.

It is further an object of the present invention to provide improved bone anchors and bone anchor inserters.

It is further an object of the present invention to provide improved bone anchors and bone anchor inserters for treatment of female urinary stress incontinence and for other medical applications.

It is further an object of the present invention to provide improved methods for treatment of urinary stress incontinence.

It is further an object of the present invention to provide improved methods for treatment of urinary stress incontinence including per vaginal bone anchor insertion into the pubic bone. These bone anchors are preferably either in the form of staples or screws. The bone anchor inserter has either a non-linear (e.g. a "C" or "V" shape) or a linear shape and is operated either by an impact or by a rotational movement to insert a staple or screw into the bone with or without vaginal wall incision.

It is further an object of the present invention to provide improved methods for treatment of urinary stress incontinence by per vaginal bone anchor insertion into the pubic bone.

It is further an object of the present invention to provide improved methods for treatment of urinary stress incontinence by per vaginal bone anchor insertion into the pubic bone and the use of a sling procedure.

It is further an object of the present invention to provide improved methods for treatment of urinary stress incontinence by the suspension of the bladder neck by pervaginal bone anchor insertion into the pubic bone and the use of a nonlinear inserter and a sling procedure.

It is further an object of the present invention to provide improved methods for treatment of urinary stress incontinence by per vaginal suspension of a sling from the pubic bone.

The invention also provides bone anchors, such as staples and screws, having suture thread secured thereto, for ejection by bone anchor insertion devices, including, but not limited to, those described herein, and for use in accordance with medical procedures.

Further features and advantages of the invention will be apparent in conjunction with the description and the drawings.

BRIEF DESCRIPTION OF THE DRAWINGS

The invention is herein described, by way of example only, with reference to the accompanying figures, wherein:

FIG. 4 is an enlarged sectional view of the staple guide in the bone anchor inserter device of FIG. 1.

FIG. 5a is an end view illustrating the staple guide of FIG. 4; FIG. 5b is similar to FIG. 5a, illustrating a modification in the construction of the staple guide.

FIGS. 6, 7a, and 7b are views similar to FIGS. 4, 5a, and 5b, respectively, illustrating a modification in the construction of the staple guide.

FIG. 8 illustrates various stages in applying the staple and thread of FIGS. 2 and 3 to the pubic bone when a procedure for treating urinary stress incontinence is performed (or for insertion into other bone when treating other conditions).

FIG. 12b is a bottom, back, and left side perspective view (on a different scale) of the stapler or pusher/impact type bone anchor inserter of FIG. 12a.

FIGS. 12d(1)–12d(6) are front views of bone screws for use in the screwdriver-type bone anchor inserter of FIG. 12c. Several different bone screw embodiments are shown, in accordance with the present invention.

FIG. 20 is a bottom, front and left side perspective view of one form of a bone anchor, a staple, used with the stapler/bone anchor inserter described herein.

FIG. 21 is a front view of the stapler type bone anchor shown in FIG. 20 which can be used with the staple inserter. In this figure, one example of a bone anchor with an offset tip is shown, i.e. a bone anchor in which the central, longitudinal axis of the tip is offset from the central, longitudinal axis of the bone anchor's shaft or body. An offset tip can be provided to a staple type bone anchor or to a screw type bone anchor to protect the suture from accidentally becoming severed during implantation.

FIG. 22 is a front view of the curved shape that a bone anchor (e.g. that shown in FIGS. 20 or 21) can achieve after insertion into bone, a consequence of it having been formed of shape memory alloy and the temperature of the staple having changed to its state changing temperature.

DETAILED DESCRIPTION OF THE DRAWINGS AND THE PREFERRED EMBODIMENTS

Figure 1:
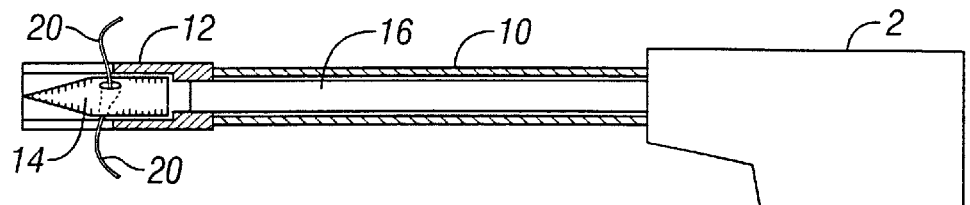
FIG. 1 illustrates one form of a bone anchor inserter device constructed in accordance with the present invention.

The stapler device illustrated in FIG. 1 comprises a housing, generally designated 2, including a handle 4 which is manually grippable by the user. The illustrated stapler device may be pneumatically powered and therefore includes a connector 6 at the bottom of the handle 4 for attaching a tube 8 connectible to a source of pressurized air. Housing 2 further includes an elongated barrel 10 having a staple guide 12 at its end for enabling the staple 14 to be ejected. Ejection of the staple 14 is effected by an ejector pin 16 which is driven into sharp impact against the base of the staple 14 by the air pressure supplied from the pressurized air tube 8. Handle 4 includes a trigger 18 which, when depressed, applies an air pressure pulse to ejector pin 16 to cause it to impact against the base of staple 14 and thereby to eject the staple out through the end of guide 12. Insofar as described, such staple devices are known, and therefore further details of its construction and operation are not set forth.

As distinguished from the known constructions, the staple 14 ejected from the guide 12 at the end of barrel 10 in FIG. 1 has a suture thread 20 secured to the staple and ejected with it. In the above-described application, the staple is driven per vaginally into the patient's pubic bone, and the thread 20 may then be used for securing the bladder neck and proximal urethra.

The staple 14 in FIG. 1 is made, in one embodiment, of elastic material. The staple is preferably shaped into the curved form illustrated at 14' in FIG. 2 while it is in its "normal" condition, and is deformed into the straight form shown at 14" in FIG. 3 while in a stressed condition. It is loaded into the stapler and ejected therefrom while in its straight stressed condition. After it has been so ejected, it returns to its curved form shown at 14' in FIG. 2, thereby better securing the staple to the bone tissue which it penetrated when it was ejected from the staple guide 12.

Figure 2:
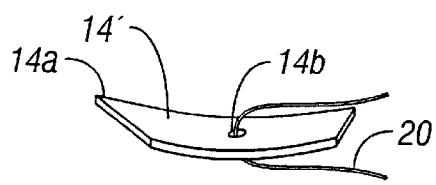
FIGS. 2 and 3 illustrate the natural curved shape and the temporary straight shape respectively, of one form of staple with attached thread in accordance with the present invention.
Figure 3:
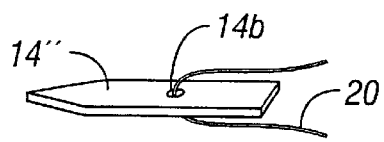

As shown in FIGS. 2 and 3, the staple 14 is formed with a pointed end 14a to enable it to penetrate the bone, and with a hole 14b approximately midway of its length for receiving the thread 20, similar to the manner in which a thread is received in the eye of a needle.

Figure 12A:
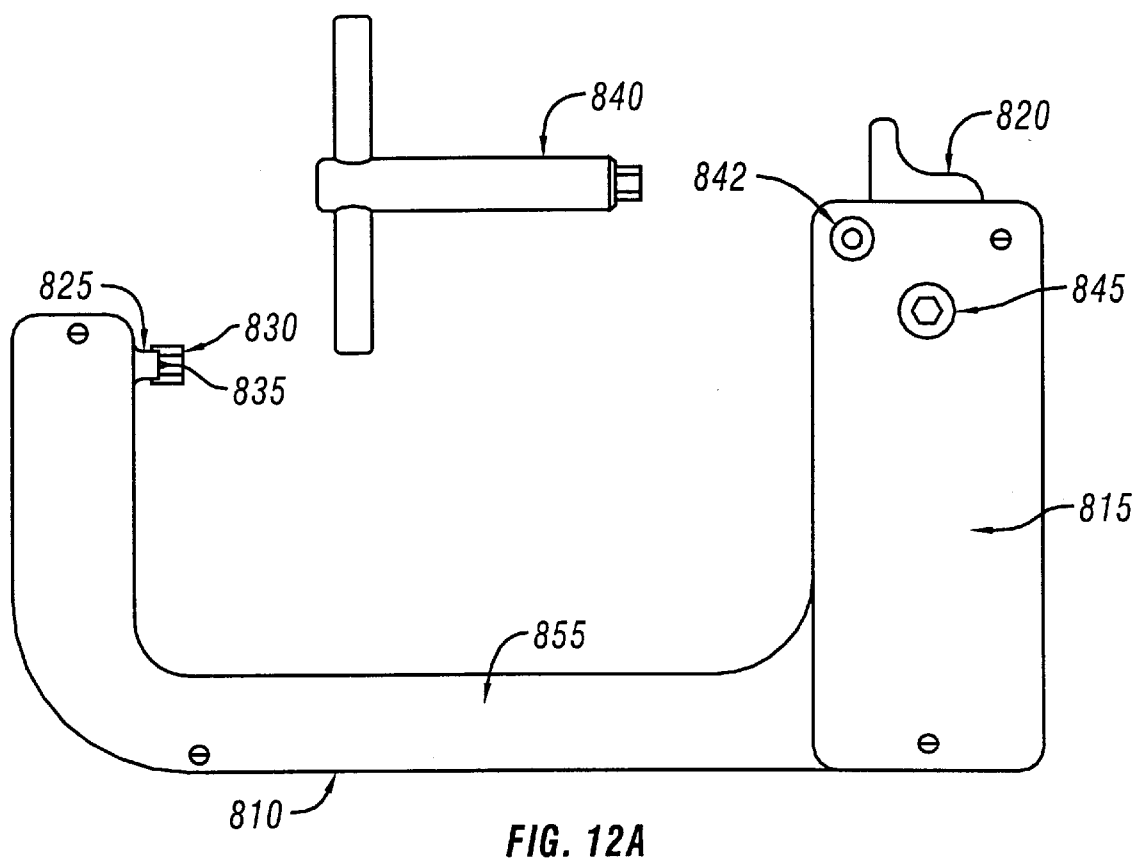
FIG. 12a is a left side view of a stapler or pusher/impact type bone anchor inserter, in accordance with the present invention, with a front view of a loading key shown as well.
Figure 12B:
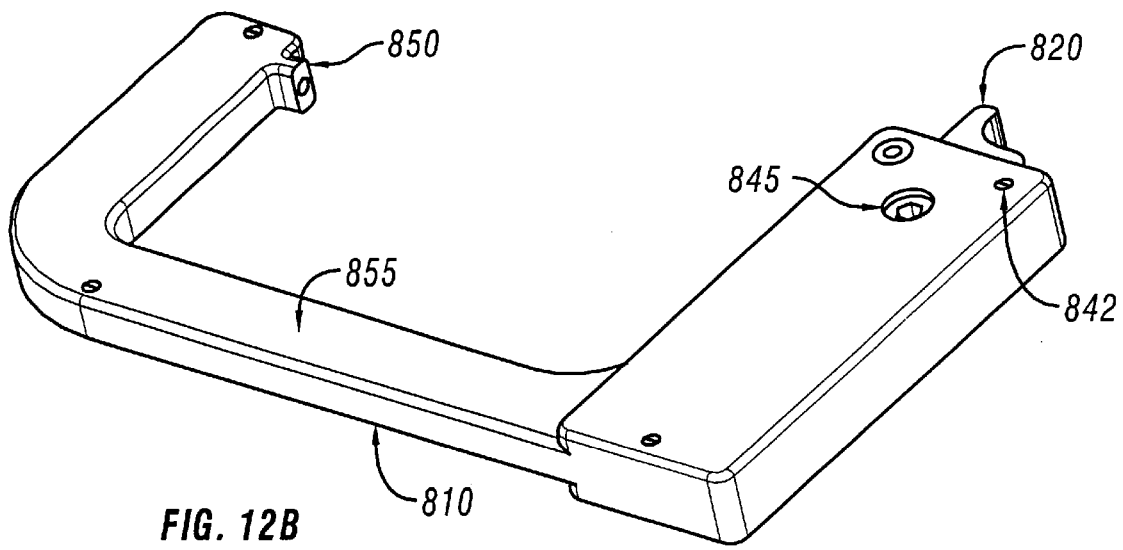
Figure 12C:
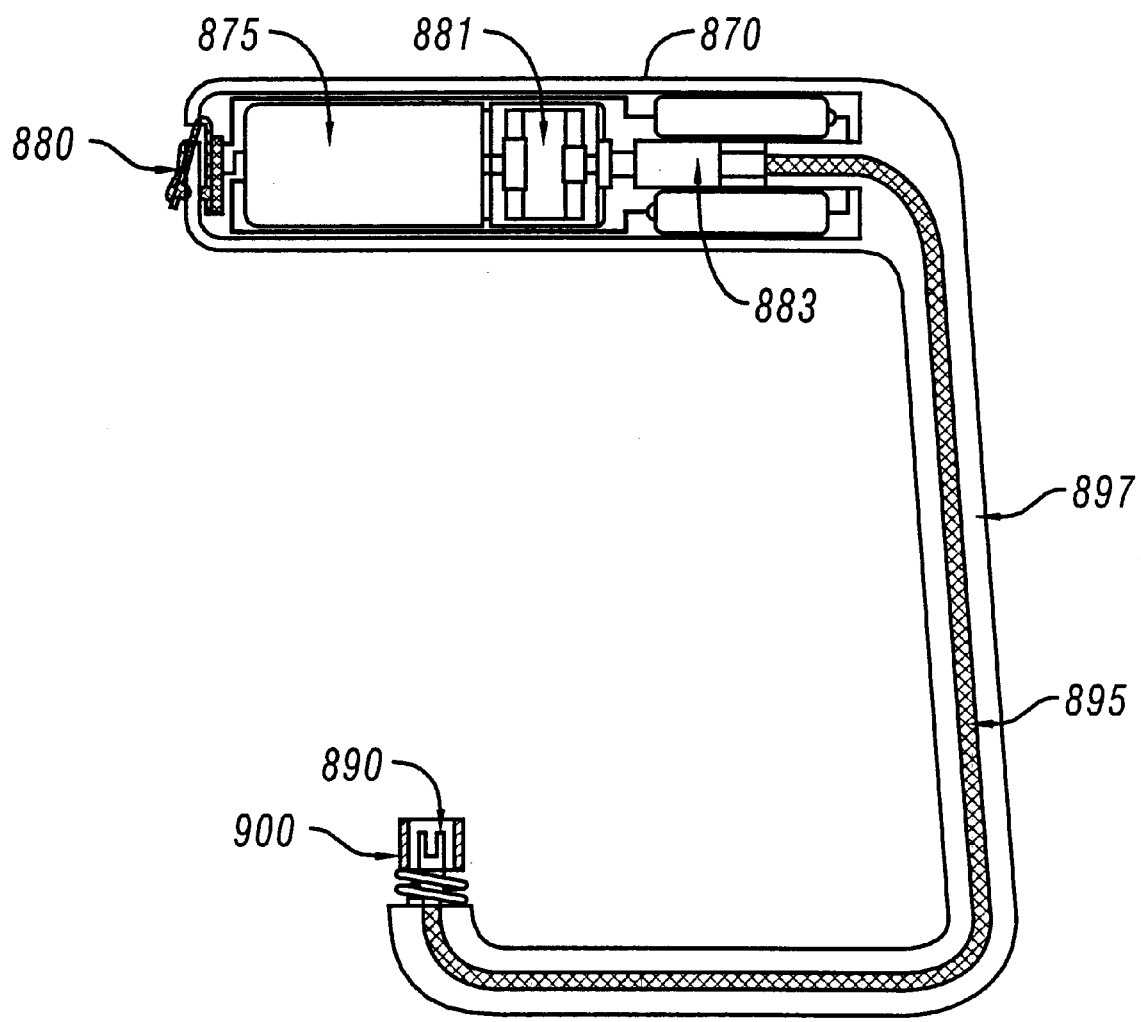
FIG. 12c is a right cross-sectional view of a screwdriver-type bone anchor inserter for rotational insertion of bone screws.
Figures 1, 2, 3, 4, 5, 6, 12D:
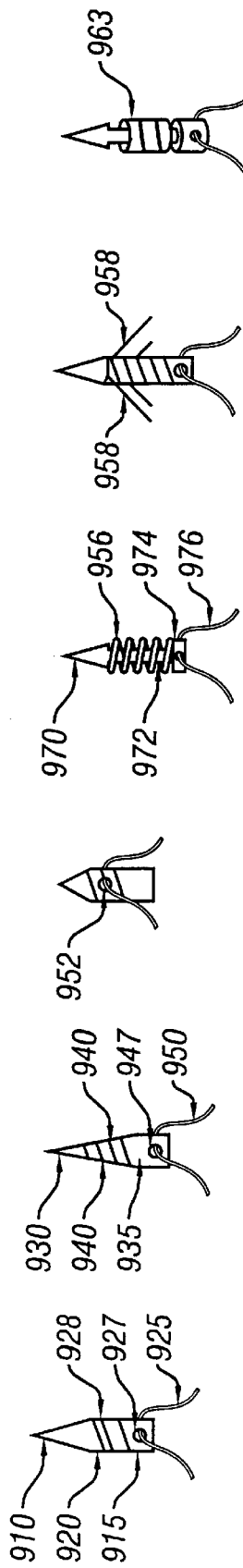

FIGS. 4 and 5 more particularly illustrate the staple guide 12 from which the staple 14, including its attached thread 20, is ejected. As shown, this guide is formed with a pair of slots 22 to accommodate the thread 20. Thus, when the base 14c of staple 14 is impacted by the ejector pin 16, the thread 20 moves through slot 22, thereby permitting the staple guide 12 to snugly fit around the ejected staple 14.

FIGS. 6 and 7 illustrate a modification in the construction of the staple guide 12 in order to accommodate the thread 20 secured to the staple 14. In the modification of FIGS. 6 and 7, the inner surface of the staple guide 12 is formed with a pair of recesses 22a for receiving the two sides of the thread 20.

The manner of using the illustrated stapler device will now be described particularly with reference to FIGS. 8a–8e.

Thus, the staple 14, together with its attached thread 20, is loaded into the staple guide 12 while the staple is in its straight condition as illustrated at 14" in FIG. 3. Depressing trigger 18 causes a high-pressure pulse of air to be applied to ejector pin 16. This pulse causes ejector pin 16 to impact against the end face 14c of the staple 14, thereby driving the staple into the bone as shown in FIGS. 8a and 8b. As soon as the staple penetrates the bone, it starts to return to its normal, curved shape as shown in FIGS. 8c and 8d. The staple is thus firmly anchored to the bone with its attached thread 20 extending through the opening formed by the staple through the bone, as shown in FIG. 8e.

Figure 9:
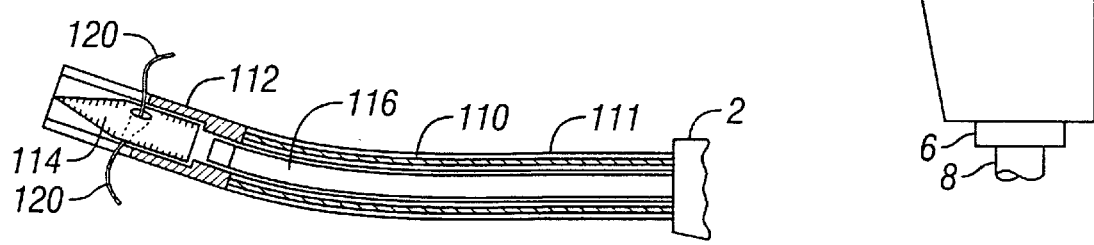
FIGS. 9–11 illustrate modifications in the construction of the bone anchor inserter device of FIG. 1.
Figure 10:
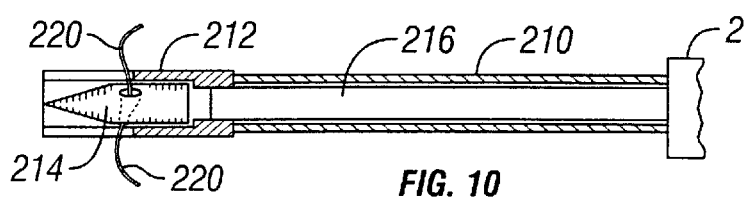

The stapler barrel 10 in FIG. 1 is preferably of a flexible plastic tube. FIG. 9 illustrates a variation wherein the stapler barrel is in the form of a closed helical wire 110 enclosed within a thin flexible tube 111, which increases the flexibility of the barrel and thereby facilitates its placement at the proper direction. FIG. 10 illustrates a variation wherein the barrel, therein designated 210, is a stiff or rigid tube.

Figure 11:
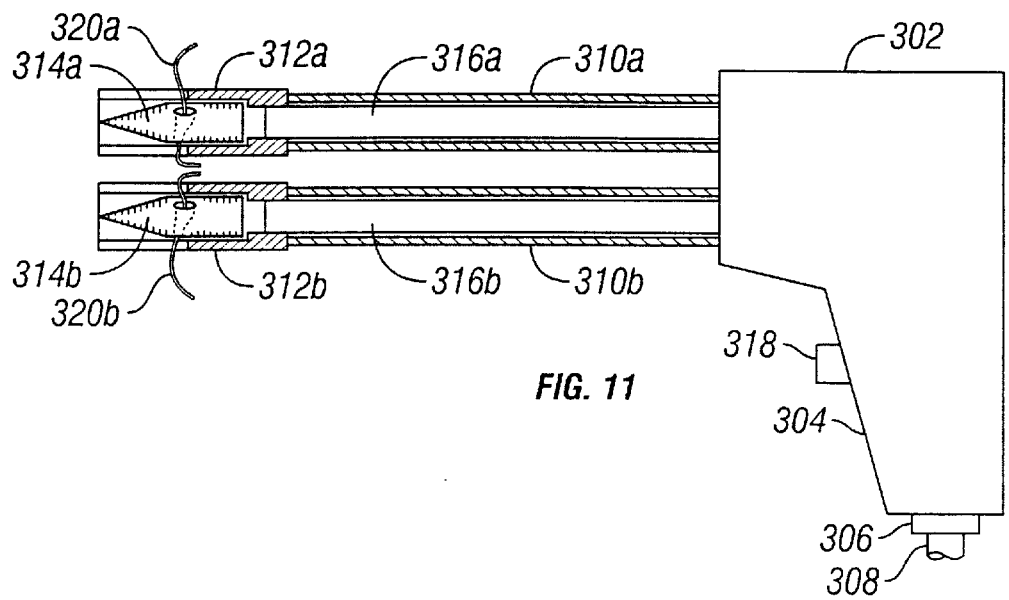

FIG. 11 illustrates a further variation wherein the stapler, therein designated 302, includes two barrels 310a, 310b in parallel relation to each other to enable two staples with attached threads to be ejected at the same time. In the modification illustrated in FIG. 11, each of the staple guides 321a, 312b receives a staple-thread unit 314a, 314b ejected by an ejector pin 316a, 316b received in the respective barrel, and both ejector pins are driven at the same time by high pressure pulses produced upon depression of the trigger 318.

The present invention also relates to an improved inserter device (whether a stapler or screw inserter) for inserting a bone anchor (whether staple or screw) into a patient, wherein the inserter device is non-linear. In one embodiment, the inserter is shaped in a "C" shaped design which allows the physician's pulling force to press the staple or screw into the bone before and during ejection or screwing of a bone anchor. As a consequence, the physician is able to use a pulling force against the resistive force of the pubic bone rather than a pushing force against the recoil of the inserter. The device also allows the physician to use the weight of a patient's body as counterbalancing leverage to minimize recoil of the staple during ejection of a staple into the patient's body. In addition, the novel geometry of the inserter allows the physician to hold the inserter and perform a per vaginal procedure with one hand out of the vagina.

As shown in FIGS. 12a and 12b, a stapler or bone anchor inserter 810 is disclosed having a handle 815, trigger 820, anchor housing 825 and an anchor shield 830. Handle 815 is attached to body 855 of the bone anchor inserter 810. Body 855 is curved such that when attached to the handle 815 the two components form a "C" shaped apparatus. The inserter can be formed as a V-shape or another non-linear configuration.

In use, a drive pin (not shown, but located within the body) forces the anchor 835 (See FIG. 20, without suture thread shown, for ease of illustration) out of anchor housing 825 and anchor shield 830 (see FIG. 12a) of the stapler 810. The stapler or bone anchor inserter 810 may be made of any suitable material, for example, stainless steel which meets surgical instrument standards. An internal spring mechanism (not shown in FIG. 12a or 12b) is in mechanical contact with the ejector pin (which is placed in contact with the bone anchor or staple). Upon the activation of the trigger 820, the ejector pin comes into contact with the bone anchor or staple 835, providing the forcible ejecting, pushing and implanting of the bone anchor or staple 835, with attached suture thread, into bone. The ejection mechanism is activated by the trigger 820 which can be provided with a safety release or lock-out 842 to prevent accidental, premature staple discharge.

The tail end of the anchor 835 (best seen in FIGS. 20–22) is held in a nearly straight configuration within anchor housing 825 until ejection. The anchor housing 825 is attached to the inserter 810 prior to use, remains attached to the inserter during anchor insertion and, after insertion of the bone anchor, is disposable, with a new anchor housing with anchor being installed onto the inserter. A retractable anchor shield 830 surrounds and protects the sharp conical front end of the anchor, to ease insertion. The bone anchor 835 (the specific anchor 844 is shown in FIGS. 20–22) is implanted into the bone without pre-drilling of a hole in the patient's bone. After cocking the internal spring mechanism using a loading key 840, which is placed into and rotated within loading socket 845, and attaching a bone anchor housing 825 (with suture attached to anchor 835 or 844), the bone anchor inserter 810 is ready for use. The spring mechanism stores the mechanical energy necessary to eject and insert the anchor into bone. In one preferred embodiment, this is approximately 2.95 Joule±10%.

FIG. 12c illustrates a C-shaped bone anchor driver in a shape allowing rotational insertion of a bone screw into a bone through a body orifice such as the vagina. The inserter consists of a handle 870 having an internal battery 875, a battery-operated rotating motor 881, with a finger switch 880 to control operation. The motor's rotational movement is linked to a shaft adapter 883 to allow more torque with less speed of rotation. The rotational power is transferred from the gear box through the inserter device to the screw adapter 890, via a flexible, rotatable shaft 895, and a flexible shaft guide 897 may be provided, as well, if desired.

The anchor, in this case, a screw, is connected to screw adapter 890, which is at the second end of the inserter, the end opposite the handle. The anchor or screw is disconnected from the inserter once the screw is implanted into the bone surface. The screw protector or retractable shield 900 shields the sharp tip of the screw until it is well positioned, so as not to accidentally damage the patient's tissue. Once the inserter is well positioned, pulling the handle 870 retracts the spring-biased screw protector or retractable shield 900 thereby allowing the screw's sharp tip to penetrate the soft tissue. In another embodiment, the screw protector or retractable shield 900 may have a rough edge surface, or small pins or sharp tips to hold the soft tissue (such as vaginal mucosa) and to prevent surrounding tissue rotation as the screw rotates and penetrates the soft tissue and into the bone. Clearly, then, depressing switch 880 activates the motor 881 which drives the flexible shaft 895 connected to the screw adaptor 890. This causes a screw (see FIGS. 12d(1)–(6)) to become embedded into the bone.

Figure 12E:
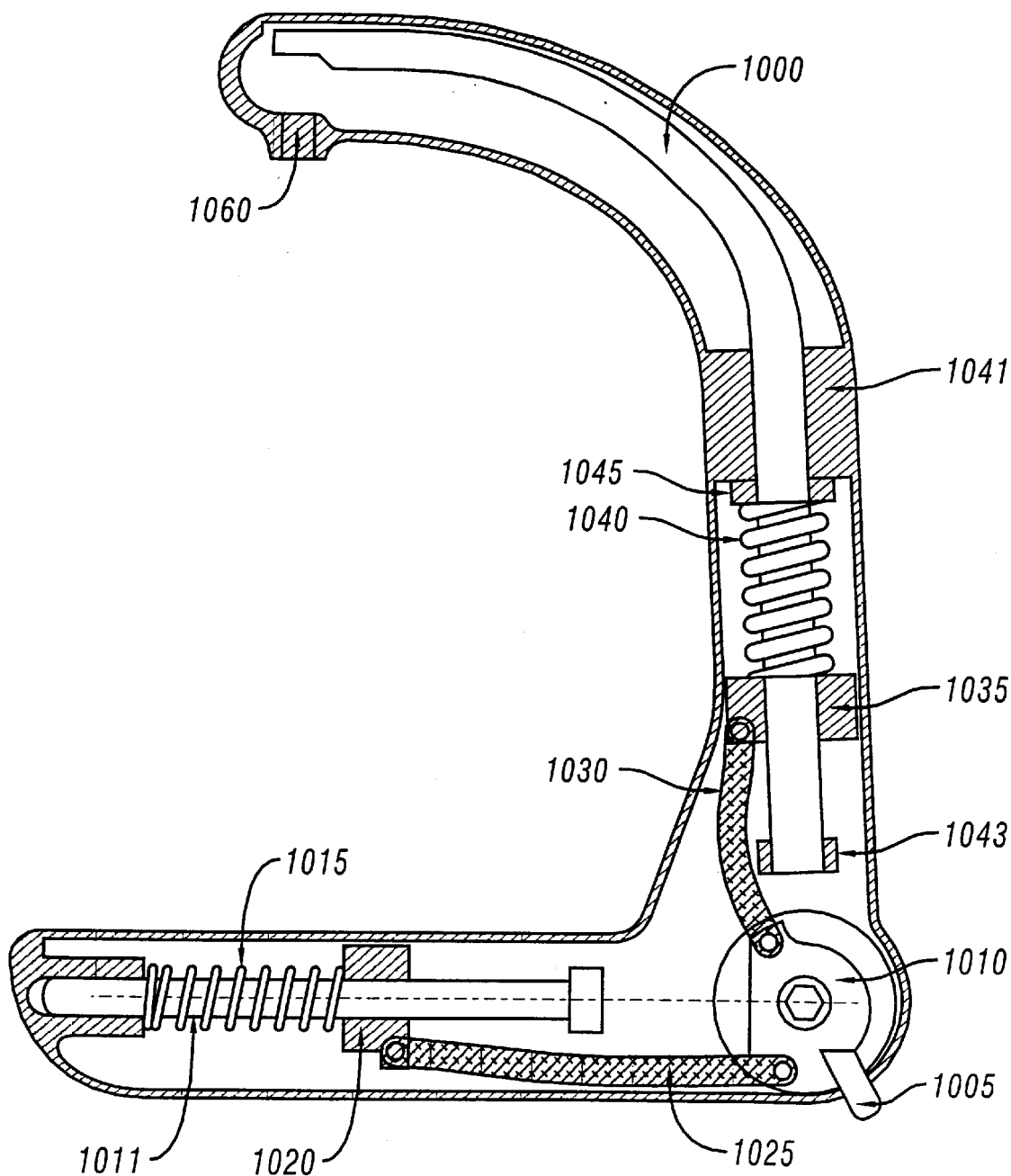
FIG. 12e is a right cross-sectional view of a spring loaded C-shaped inserter, having an alternative driving mechanism, a spring mechanism.

FIG. 12e shows an alternative, spring-loaded C-shaped inserter, having a different spring mechanism to that shown in FIGS. 12a & 12c. The inserter has a dual spring mechanism which allows the user to impart more energy and impact to the anchor during implantation into the bone. At the same time, this inserter has the significant advantage that the two spring design results in cancellation of the rotational movement that the inserter may have during release. This results in a more stable anchor insertion.

This alternative inserter embodiment utilizes a hammer 1000 which impacts and ejects an anchor into a bone. When safety 1005 is not in place blocking the movement of connecting cam 1010, second spring 1015 can expand outward from its compressed state against second weight 1020 to force second rod 1025 to the right to allow rotation of connecting cam 1010. Connecting cam 1010 is connected to both second rod 1025 and to main rod 1030. Rotation of the connecting cam 1010 in the counterclockwise direction by second rod 1025 moving to the right, as shown in FIG. 12e, moves main rod 1030 away from its locking or "up" position against main weight 1035 which allows the spring 1040 to expand to cause hammer 1000 to impact a bone anchor.

More specifically, while main rod 1030 is forced against main weight 1035, the hammer 1000 is maintained in a stationary position and primed for subsequent movement to eject a bone anchor held in recess 1060. Main spring 1040 is connected to main weight 1035, with main weight 1035 slidably connected to hammer 1000. A friction disk 1045 is provided above main spring 1040. A hammer guide 1041 is provided around a portion of the hammer 1000, as shown in FIG. 12e. Before activation of the inserter, main spring 1040 is maintained in a compressed position. Movement of main rod 1030 downwardly, with main weight 1035, allows main spring 1040 to expand outward, forcing main weight 1035 to be slammed against ring 1043, secured to the end of the hammer. This causes hammer 1000 to rapidly move downward. The release of the energy stored in main spring 1040 thus forces hammer 1000 downward to impact and eject a bone anchor out of recess 1060 and into a bone.

FIGS. 13–19 illustrate other constructions of staple-thread units which may be used.

Figure 13:
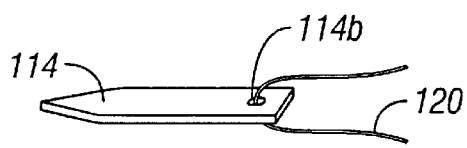
FIGS. 13–19 illustrate other forms of staple- thread units which may be used in accordance with the present invention.

The unit illustrated in FIG. 13 includes a staple 114 and a thread 120 similar to the construction illustrated in FIGS. 2 and 3, except that the hole 114b through which the thread 120 is passed is at the rear end of the staple, rather than at the middle.

Figure 14:
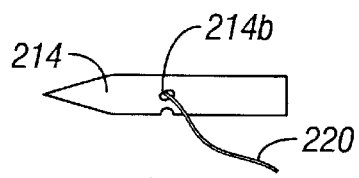
Figure 15:
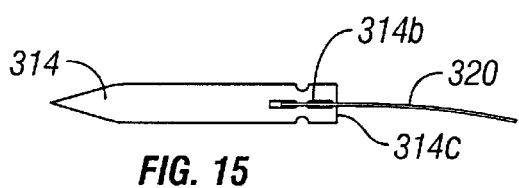
Figure 16:
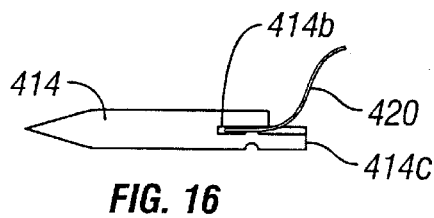

FIG. 14 illustrates a construction wherein the staple 214 is provided with a bore 214b extending at an angle to the longitudinal axis of the staple 214 with the end of the thread 220 received and fixed therein by crimping the staple. FIG. 15 illustrates a construction wherein the bore 314b is in the base 314c of staple 314 and extends along or parallel to the longitudinal axis of the staple 314, the thread 320 being received within the bore 314b and fixed therein by crimping the staple. FIG. 16 illustrates a construction similar to that of FIG. 15, except that part of the base 414c of the staple 414, formed with the axial bore 414b for receiving the thread 420, is cut away so that the impact of the ejector pin against the base of the staple will not impact against the end of the thread.

Figure 17:
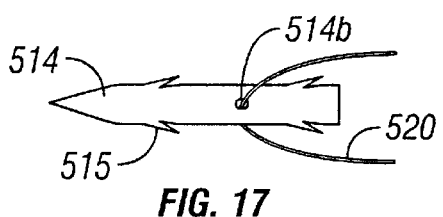

FIG. 17 illustrates a further variation wherein the staple 514 is formed with a plurality of barbs 515 projecting from its outer surface, to fix the staple to the bone into which it has penetrated. The thread 520 is passed through a hole 514b in the staple.

Figure 18:
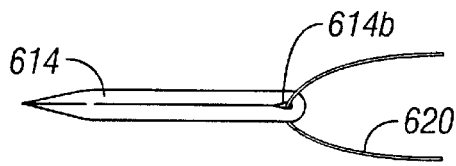
Figure 19:
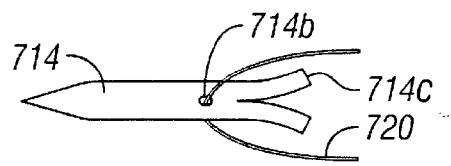

FIG. 18 illustrates a staple made of bent wire. FIG. 19 illustrates a staple with a split tail 714c, which is straightened under stress when first inserted into the staple guide 12 and splits after ejection, a consequence of its shape memory.

In one recommended embodiment, the bone anchor can be made of a single piece of a shape memory alloy, such as the nickel-titanium alloy called Nitinol. One form of bone anchor, for example, which can be used with the present invention, has a conical front end 846 (See FIGS. 20–22) with diameters ranging from 1.9–2.4 mm, and a tail end with a nearly rectangular cross-section. The tail portion is preferably 6.0 mm long with a width that ranges from 1.9–2.4 mm and a thickness of about 0.6 mm. The anchor tail 844 contains two holes 848 and 850 which are used for threading the suture. An example of a suture thread which can be used in the bone anchor is sterile polypropelene monofilament No. 1. The bone anchor is depicted in FIGS. 20 through 22. According to the preferred embodiment of the bone anchor 835, the longitudinal axis of the tail end is offset from the center axis of the conical tip 846. This is best seen in FIGS. 21 and 22.

Within the bone medulla, the bone anchor 835 soon heats to body temperature, changing by the characteristics of shape memory alloy, for example, from a straight to a curved shape, i.e., the longitudinal axis of the anchor changes, after insertion. This is shown in FIG. 22. According to one preferred embodiment, the end of the tail and the rear end of the conical tip, after heating of the bone anchor sufficient to change its shape, will subtend an angle of about 75°±16° (as seen in FIG. 22). This change of shape is because of the fabrication of the anchor from shape memory alloy. This curved shape facilitates fixation of the anchor within the bone and inhibits the inadvertent removal of the anchor. Pulling on the suture, which is connected to the anchor 835, causes the anchor to rotate within the bone and further fixate in the bone. The reformation of the anchor to its curved shape (the shape it had prior to straightening by being held in the anchor housing 835) and rotation, together, prevent the anchor from inadvertently exiting through the entrance path provided into the bone. The small profile and sharpness of the anchor tip 846 allow easy insertion into the bone with minimal damage to the bone surface.

Thus, the present invention provides an apparatus and method which (in the anchor ejection or screwing mode) does not require pre-drilling of the bone or soft tissue dissection to insert the bone anchor into the bone. Similarly, the bone anchor does not require cement or other fixative to remain in place.

The bone anchor and bone anchor inserter are supplied sterile. As the bone anchor inserter is a multiple use device, the inserter (and its loading key) should, of course, be cleaned and sterilized before each new patient procedure. Cleaning is accomplished by washing and rinsing the inserter and loading key with water and a liquid detergent, while scrubbing with a flexible brush to completely remove all traces of blood. The inserter and loading key should be rinsed thoroughly with water to remove detergent residues. Panels in the inserter body allow access for cleaning. Once cleaned, the inserter and loading key may be cloth or air dried. The inserter and loading key may be sterilized by heat or steam autoclave, or gas (EtO), in accordance with hospital procedures for sterilization of stainless steel surgical instruments.

Various different types of bone screws 920 can be used in accordance with the present invention. As shown in FIG. 12d(1), a bone screw is disclosed having a conical tip 910 and a screw body 915. The diameter of each of the screw threads 928 (the grooves, recesses or indentations in the material of the screw) is constant along the screw body. The suture 925 is attached at a hole in the end 927 of the bone screw.

FIG. 12d(2) shows a bone screw 920 with a more tapered conical tip 930 and a screw body 935. In this version, the diameter of the screw threads 940 vary. The diameters of the screw threads 940 increase from small diameters near the apex of the conical tip to greater diameters near the screw body 935. The screw threads 940 can be located on all or a portion of the screw body as well, if desired. The suture 950 is attached through a hole in the end 947 of the screw.

FIG. 12d(3) is similar to FIG. 12d(1). In this figure, however, the suture is shown attached through a hole in the middle 952 of the bone screw.

FIG. 12d(4) shows a bone screw 920 in which the screw threads or grooves are formed by wrapping spring wire 956 around a solid body. The body has a leading tip 970 and a shaft 972, of smaller relative cross section. A trailing end 974 with a hole is provided for attaching the suture thread 976. The spring wire is wrapped on the shaft 972 and maintained between leading tip 970 and the trailing end 974.

FIG. 12d(5) shows a bone screw similar to that in FIG. 1d(4). In this screw, leaf springs 958 are provided. Leaf springs 958 are initially flattened against the side surface of the bone screw, i.e., when the screw is inserted into the bone. Upon insertion, however, the leaf springs 958 expand outward from a compressed to a non-compressed state (due to the elasticity which is characteristic of a spring) to provide greater anchoring of the bone screw within the bone.

FIG. 12d(6) discloses a bone screw in which the screw threads or grooves are formed by wrapping a spring plate 963 around the screw body or shaft of the screw. Here, too, the spring plate is held between the leading tip and the trailing end.

The bone screw is typically made of a medical grade alloy such as Stainless Steel 316. Its sharp tip and small diameter allows for its penetration through the vaginal wall and the periosteum, without pre-drilling a hole. As the screw is rotated by the inserter, which may be linear, C- or V-shaped, it further enters the bone until it reaches a prescribed depth within the bone. The screw then automatically disconnects from the rotating inserter shaft. The medical technique of inserting a bone screw into the pubic bone through the vagina for the purposes of bladder neck suspension is also within the scope of the present invention, as is the bone screw inserter.

While the invention has been described with respect to one particular application, it will be appreciated that the described anchor device and anchor-thread units may be used for other applications, e.g., for shoulder dislocations, endoscopic operations, or the like. The anchor inserter may also be electrically operated and may use other mechanical impact or screw-type devices for driving the anchor. The anchors themselves may be of known bioabsorbable materials.

Following is one procedure for performing the above-described operation: A 20F urethral catheter is inserted into the bladder, and a balloon is inflated to 20 cc and retracted gently downwardly against the bladder neck. The surgeon inserts two fingers into the vagina, pressing the anterior vaginal wall with one finger on each side of the urethra, which is felt because of the inserted catheter. By pressing the fingers upwardly and backwardly, the bladder neck and proximal urethra are pressed against the posterior wall of the pubic bone. At this stage, two staples are ejected longitudinally on each side of the urethra, about 1–2 cm apart. The two threads on each side of the urethra are tied one to the the other. They may be tied on the vaginal mucosa, in which case the tension will embed the threads to the sub-mucosa after some time. Alternatively, the threads may be tied under the vaginal mucosa by passing one of the threads on the same side. The threads may be made of a monofilament non-absorbent material, as well as of an absorbent material, dependent on the preference of the physician.

Figure 23:
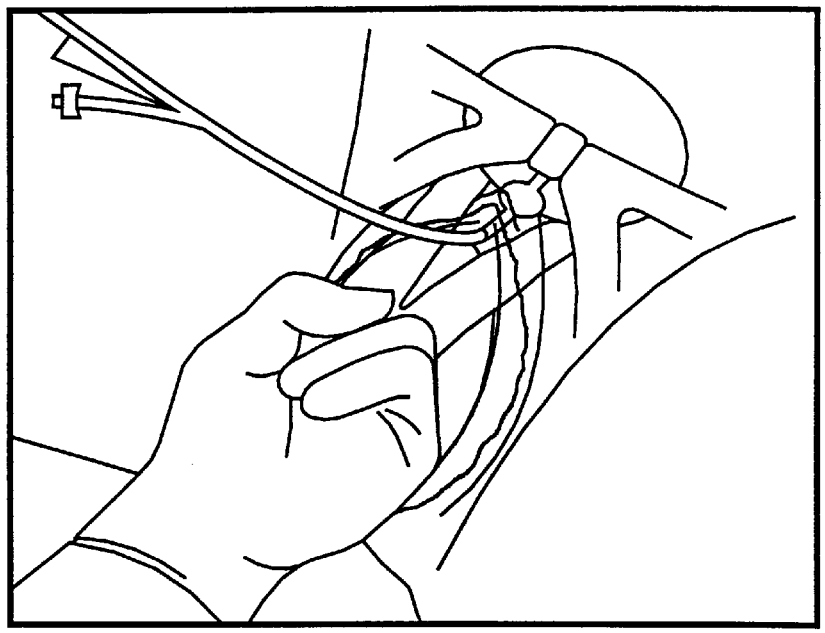
FIG. 23 is a perspective view of a catheter inserted into the bladder of a patient in accordance with the method of the present invention, with a physician's (or health care worker's) two fingers partially inserted into a woman's vagina.

Further methods of the present invention is shown in FIGS. 23–26. With the patient in lithotomy position, the surgical area and the vagina are cleaned and disinfected. A Foley catheter is inserted inside the bladder, and the balloon is inflated with approximately 10–20 cc of water. The catheter is then pulled backwardly to locate the balloon just above the bladder neck as shown in FIG. 23.

The catheter (within the urethra) and the balloon at the bladder neck are palpated by the physician's finger tips.

Figure 24:
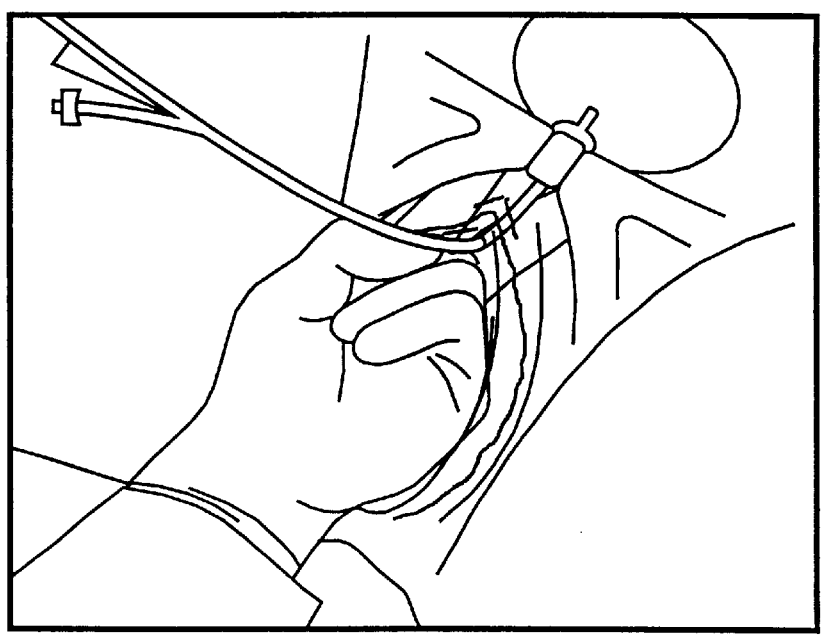
FIG. 24 is a perspective view of the hand of the physician pressing the anterior vaginal wall of a patient against the posterior of her pubic bone, according to the present method (with the catheter in place).
Figure 25:
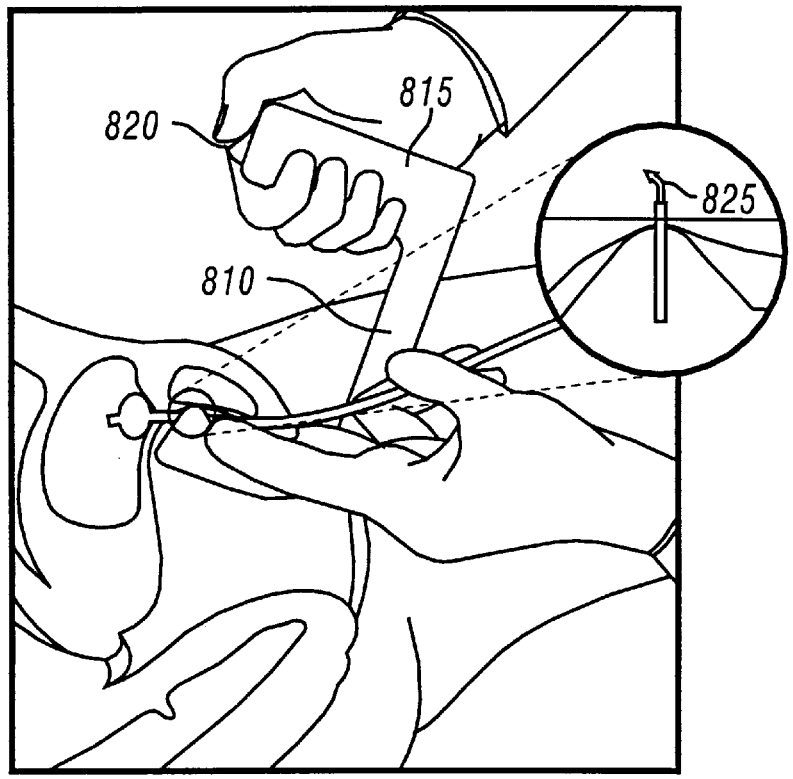
FIG. 25 is a perspective view of the non-linear bone anchor inserter (in this case, a C-shaped inserter) inserted into the vaginal canal, with the anchor housing pressing the anterior vaginal wall of the patient against her pubic bone. Notice that the physician's hand, which is used for triggering the mechanism of the inserter, is outside of the vagina and that the physician can pull the handle of the inserter against the resistive force of the pubic bone. An enlarged inset cross-sectional view is provided of the insertion step of the bone anchor into the pubic bone.

Pressing the fingers upward and forward, the anterior vaginal wall is if pressed against the posterior pubic bone surface, as shown in FIG. 24.

The bone anchor inserter (whether a stapler/impact or a screwdriver-type inserter) is then inserted into the vagina (see FIG. 25) near the bladder neck and approximately 2 cm. to the side of the urethra. The inserter is pulled against the pubic bone. Notice that the triggering hand of the physician is external to the vagina and that the force applied by the physician is one of pulling against the resistive force of the pubic bone. The tip of the bone anchor 835 touches and penetrates the vaginal wall and enters the cortex of the pubic bone.

Thus, once the inserter is stable and properly positioned in the vagina, the trigger 820 (or switch 880, for the screw inserter) is pulled and the bone anchor 835 penetrates and fixates within the bone. When the end of the inserter 810 is under the pubic bone, and pressed against it, the physician pulls up on the handle 815 of the stapler or bone anchor inserter 810. By doing so, the physician lifts the anchor 835 or screw 920 and anchor housing 825 or screw adaptor 890 against the pubic bone. A portion of the weight of the patient resists the lifting of the inserter, pressing against it firmly. As a result, the lifting of the stapler or bone anchor inserter 810 is performed against some of the weight of the patient, ensuring a firm and effective contact of the anchor tip with the pubic bone. Mechanically, it is easier for the physician to pull on the inserter with his or her hand outside of the vagina than for the physician to have his or her triggering hand within the vagina and pushing the inserter against the pubic bone. The penetration of the tip of the bone anchor into the bone cortex before ejection or screwing further increases the stability of the ejection into the pubic bone. The use of the non-linear or C-shaped inserter allows at least part of the patient's weight to counterbalance the recoil of the spring mechanism. The patient's body weight, along with the inserter's shape, provides the physician with suitable leverage for ensuring penetration of the anchor 835 or screw 920 into the pubic bone. This is especially important in the use of the present bone anchor device which, in the case of the ejected anchor, seeks to avoid pre-drilling of a hole, followed by anchor insertion.

Releasing the safety 842 first and then pressing the trigger 820 of the device activates the inserter spring mechanism (not shown) which ejects the anchor 835 to a prescribed depth within the bone (e.g. 2.5 mm) so that no portion of the anchor protrudes from the bone surface. Although the end of the inserter will experience a reaction force when the staple is ejected, the weight of the patient, pressing downward against the inserter end (anchor housing 825 and anchor shield 830) combined with the force exerted by the physician by pulling the handle 815 of the bone anchor inserter 810 upward (so that the end of the inserter is forced against the weight of the patient and the penetration of the tip of the anchor into the pubic bone before ejection) result in a firm and solid contact between the inserter and the pubic bone during and through the insertion process, minimizing any problems of insertion associated with stapler recoil.

Two to four anchors are preferably inserted into the patient. Bone anchors are inserted on each side of the urethral axis or parallel along each side of the posterior aspect of the superior pubic bone ramus, lateral to the symphysis pubis. When four bone anchors are used, two bone anchors are inserted on each side of the urethral axis or parallel along each side of the posterior aspect of the superior pubic ramus, about 2 cm. lateral to the symphysis pubis. Each pair of two bone anchors is inserted with the two bone anchors in a pair approximately 2 cm. apart. Cystoscopy is then performed to verify that there are no bladder or urethral perforations.

Figure 26:
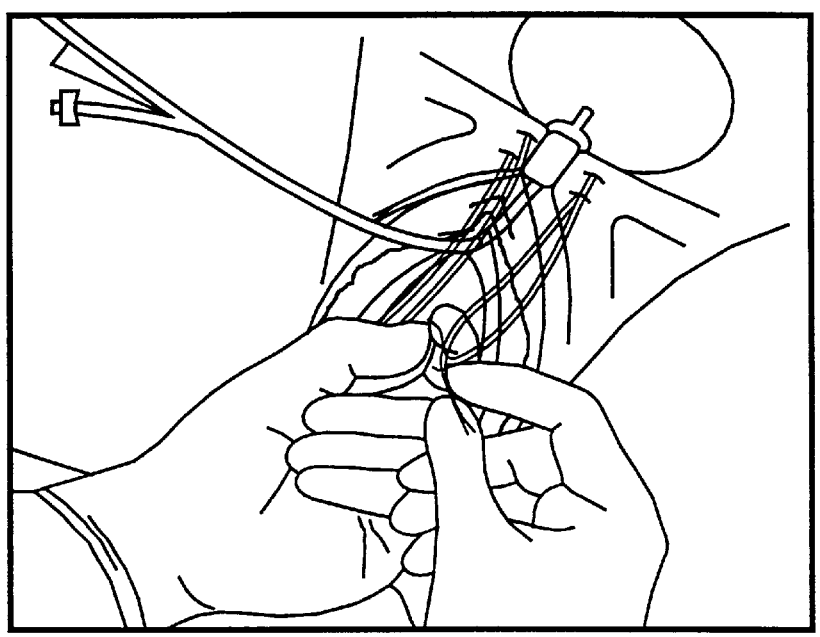
FIG. 26 is a perspective view of the hands of the physician tying the suture threads affixed to the bone anchors (the bone anchors having first been implanted into the patient's pubic bone).

The suture threads extending from the anchors are then tied. For example, when inserting four bone anchors, four sets of suture threads should protrude from the vaginal wall. The suture threads are tied from one bone anchor to the other, ipsilaterally on each side of the urethra, as shown in FIG. 26. They may be tied either above the vaginal mucosa or below the vaginal mucosa (using a deshamp) with or without vaginal dissection. The tie may be left as is or pushed beneath the mucosa.

Suprapubic or Foley urethral catheterization is then performed. The suprapubic catheter is to remain until complete bladder emptying is achieved by normal urination. Prophylactic antibiotic is administered perioperatively. Physical strain and lifting by the patient is to be avoided for approximately 2–3 months.

In cases where the urethra itself is very wide, the threads may be used for engaging and elevating the urethra to the posterior pubic bone as in a "sling operation".

Numerous different types of sling procedures can be provided, in accordance with the invention. These sling procedures are preferably provided for the treatment of urinary stress incontinence as disclosed above and herein. Alternatively, it is contemplated that they may be also useful in other medical procedures to correct other anatomic pathologies and/or relieve discomforts of a patient.

In the preferred embodiment of the invention, the sling procedure is a pervaginal procedure in which one or more bone anchors are inserted through the vaginal wall of the patient to enter the pubic bone, and in which suture thread and a sling are utilized to adjust the anatomic position of the bladder neck and the urethra of the patient, or more specifically, to suspend the bladder neck. The bone anchors may be bone screws and/or bone staples, and preferably have the suture suture thread already attached thereto before they are inserted into the vagina of the patient. In a further preferred embodiment of the invention, insertion of the anchors is conducted using a nonlinear inserter, preferably one of the inserters disclosed herein.

In a preferred embodiment, the In-Fast™ Bone Screw System and/or the In-Tac™ Bone Anchor System is used, both of which are available from Influence, Inc. of San Francisco, Calif.

Figure 27:
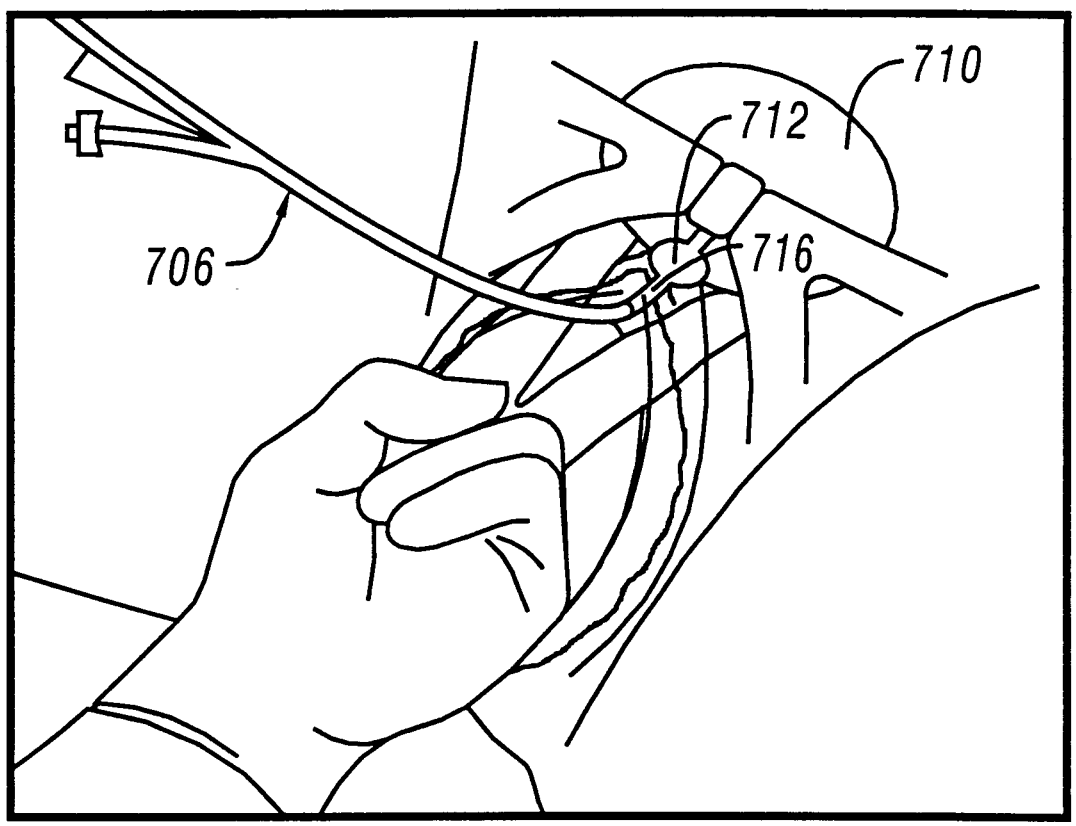
FIG. 27 is a perspective view, similar to that shown in FIG. 23, of an initial step in sling procedures of the present invention, in which a catheter is inserted into the bladder of a patient in accordance with the method of the present invention, with a physician's (or health care worker's) two fingers partially inserted into a woman's vagina. The balloon is inflated with water and located just above the bladder neck. This step is performed after a first initial step consisting of a perioperative antibiotic treatment, anaesthesia, and disinfection and cleansing of the surgical area (as are all known in the art).

In accordance with the various embodiments of the sling procedure of the present invention, the procedure is initiated by a pervaginal insertion of an anchor into the patient. After a perioperative antibiotic treatment, the patient is placed under spinal, general or local anesthesia and in the lithotomy position, and the surgical area and the vagina are cleaned and disinfected. A Foley catheter 706 is then inserted inside the bladder 710, and the balloon 712 is inflated with approximately 10–20 cc of water. The catheter 706 is then gently pulled to locate the balloon 712 just above the bladder neck 716 as shown in FIG. 27.

Figure 28:
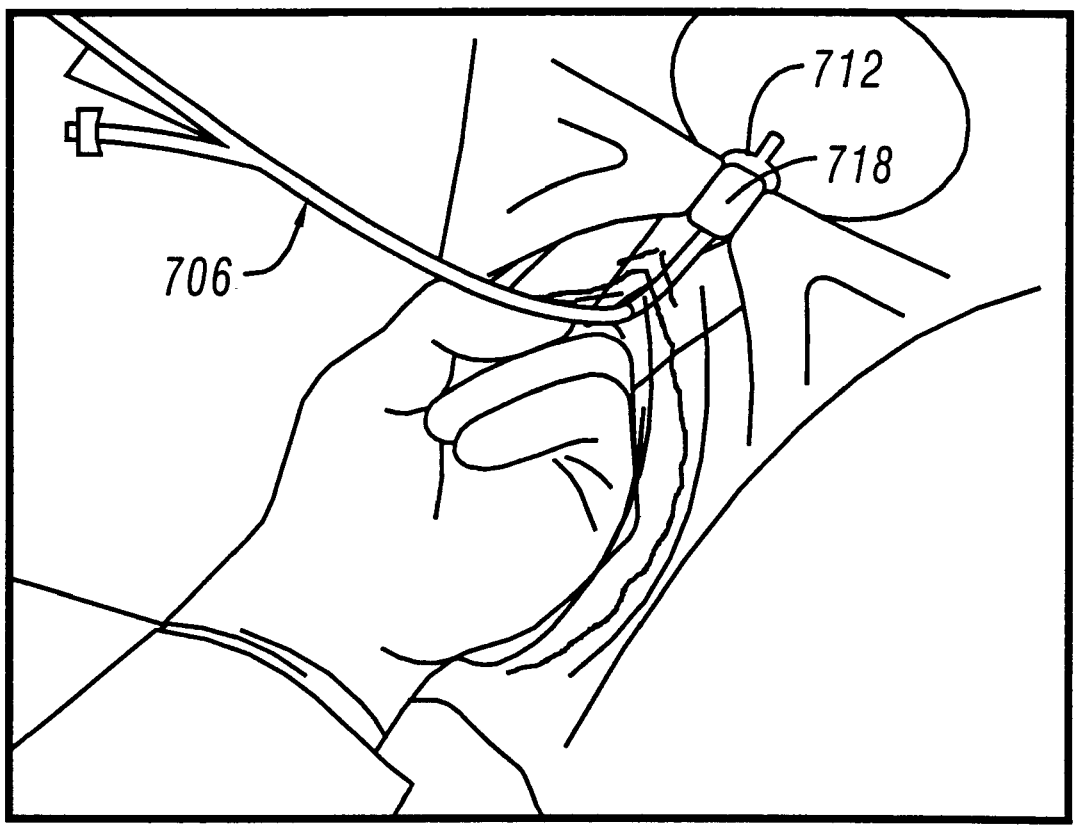
FIG. 28 is a perspective view of a subsequent initial step in the sling procedures of the present invention, similar to that shown in FIG. 24, in which the physician presses the anterior vaginal wall against the posterior pubic bone.

When the balloon 712 has been positioned, the catheter 706 is then located, within the urethra, between the physician's index and second fingers so that the finger tips are touching the balloon at the bladder neck. The physician then, by pushing his or her fingers upward and forward, presses the anterior vaginal wall against the posterior of the pubic bone 718, as shown in FIG. 28.

Figure 29:
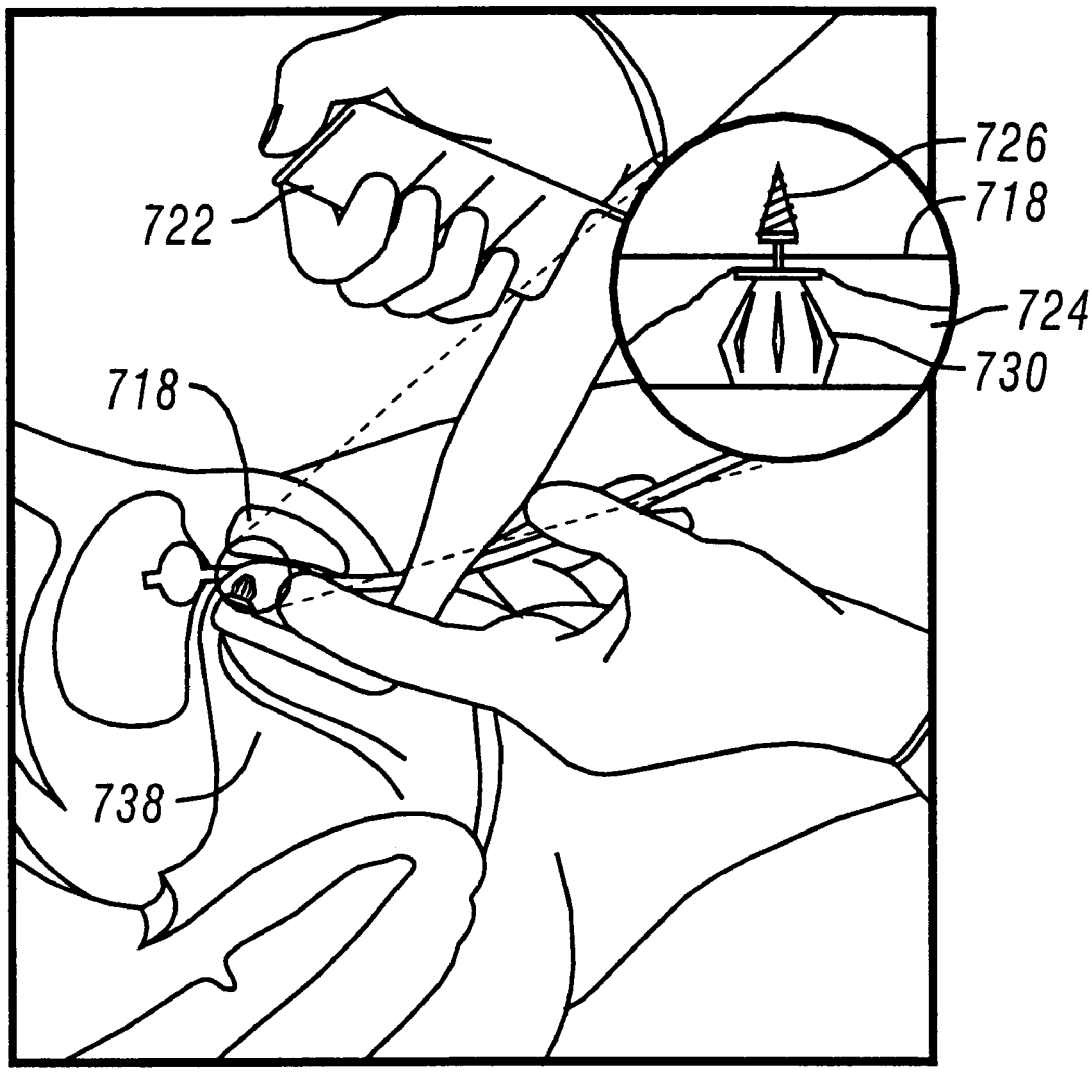
FIG. 29 is a cross sectional view of a patient, including the inserter and the physician's hands, showing a subsequent initial step in the sling procedures of the present invention, in which the anchor inserter is inserted into the vagina, and the bone anchor tip is inserted through the vaginal wall into the cortex of the pubic bone (shown enlarged in the inset of the drawing).

As shown in FIG. 29, after pressing the anterior vaginal wall 724 against the pubic bone, and while still feeling the catheter within the urethra, the physician then inserts the bone anchor insertion device 722 preferably a nonlinear bone screw inserter) into the vagina, below the bladder neck and lateral to the symphysis pubis, about 2 cm. to the side of the urethra. The inserter device 722 is then pulled upward until the screw 726 presses the anterior vaginal wall 724 against the pubic bone 718.

In the preferred embodiment, an inserter 722 is used having a retractable shield 730. Retractable shield 730 is a protective cover for the screw 726 which is designed such that the application of pressure to the shield 730 causes the shield to retract and reveal the screw. For example, the shield 730 can be flexible, such that it bends, contracts, or compresses when force is provided to it. Or, the shield 730 can rest on springs while the screw does not, so that application of pressure to the shield retracts it, while the screw remains i n place.

Once the shield 730 is pressed against the pubic bone 718, the screw shield 730 will collapse and the tip of the bone screw 726 will become exposed so as to allow it to penetrate the vaginal wall 724 and enter the cortex of the pubic bone 718, as shown in FIG. 29. The safety lock of the inserter 722 can then be released to allow deeper insertion of the screw 726 into the bone, by continuously pressing the inserter's operate button to insert the screw. When the screw 726 has been tot ally inserted (after approximately 10–20 seconds, a s indicated by change in the inserter's motor tone and cessation of twisting of protruding suture), as shown in the exploded view of FIG. 29, the operate button is released and the inserter can be removed from the vagina for reloading.

Once the first anchor (preferably a screw) has been inserted into a patient, various embodiments are available for the methods of the invention. In accordance with the invention, a submucosal tunnel technique or an anterior wall dissection technique can preferably be performed, as disclosed below.

Submucosal Tunnel Technique

Figure 30:
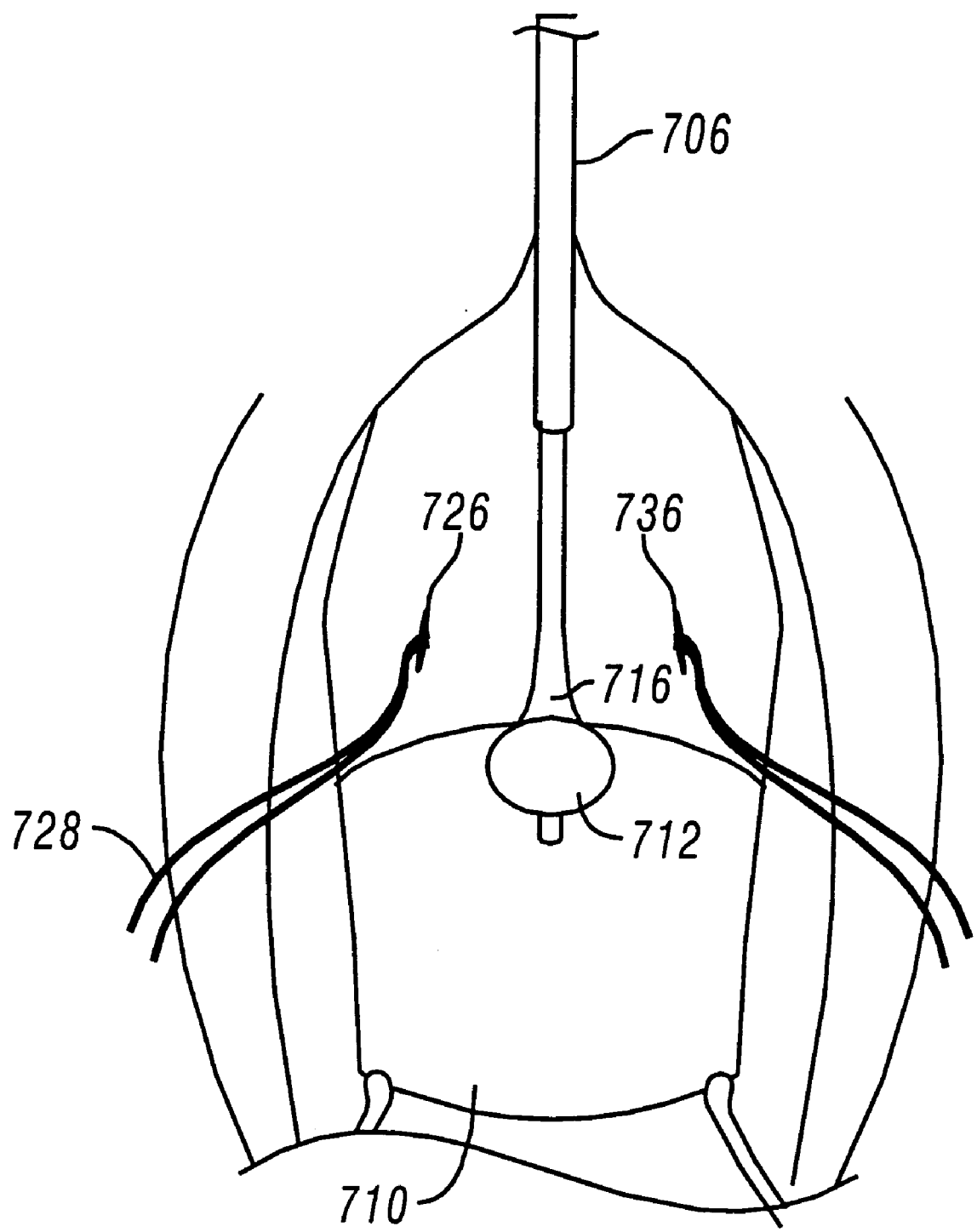
FIG. 30 is a cross sectional view of a patient's vagina showing a first step in the submucosal tunnel technique of the sling procedures of the present invention, in which a second screw is inserted on the contralateral side of the urethral axis, which step is performed after the initial preparatory steps shown in FIGS. 27–29.
Figure 31:
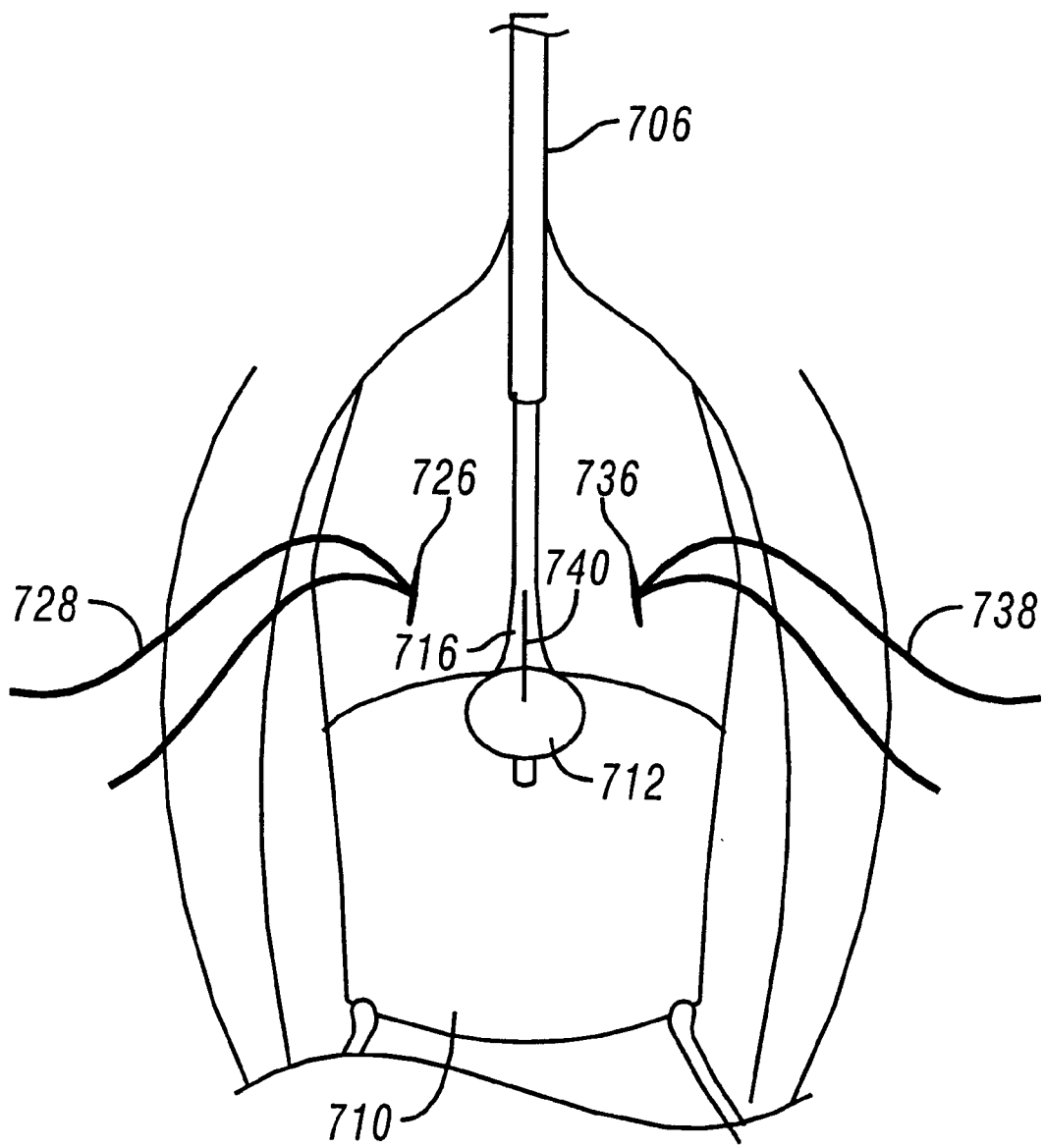
FIG. 31 is a cross sectional view of a patient's vagina showing a subsequent step in the submucosal tunnel technique of the sling procedures of the present invention, in which a midline incision is cut in the anterior vaginal mucosa, just below the bladder neck.

In accordance with the submucosal tunnel technique, once the first screw 726 has been inserted, a second screw 736 is inserted in the same elevation as in the first, on the contralateral side of the urethral axis, as shown in FIG. 30. When the second screw 736 is in place, a cystoscopy is performed to verify bladder and urethral integrity. A midline incision 740 (see FIG. 31) about 1.5–2 cm long is then cut in the anterior vaginal mucosa, just below the bladder neck 716 as shown in FIG. 31.

Figure 32:
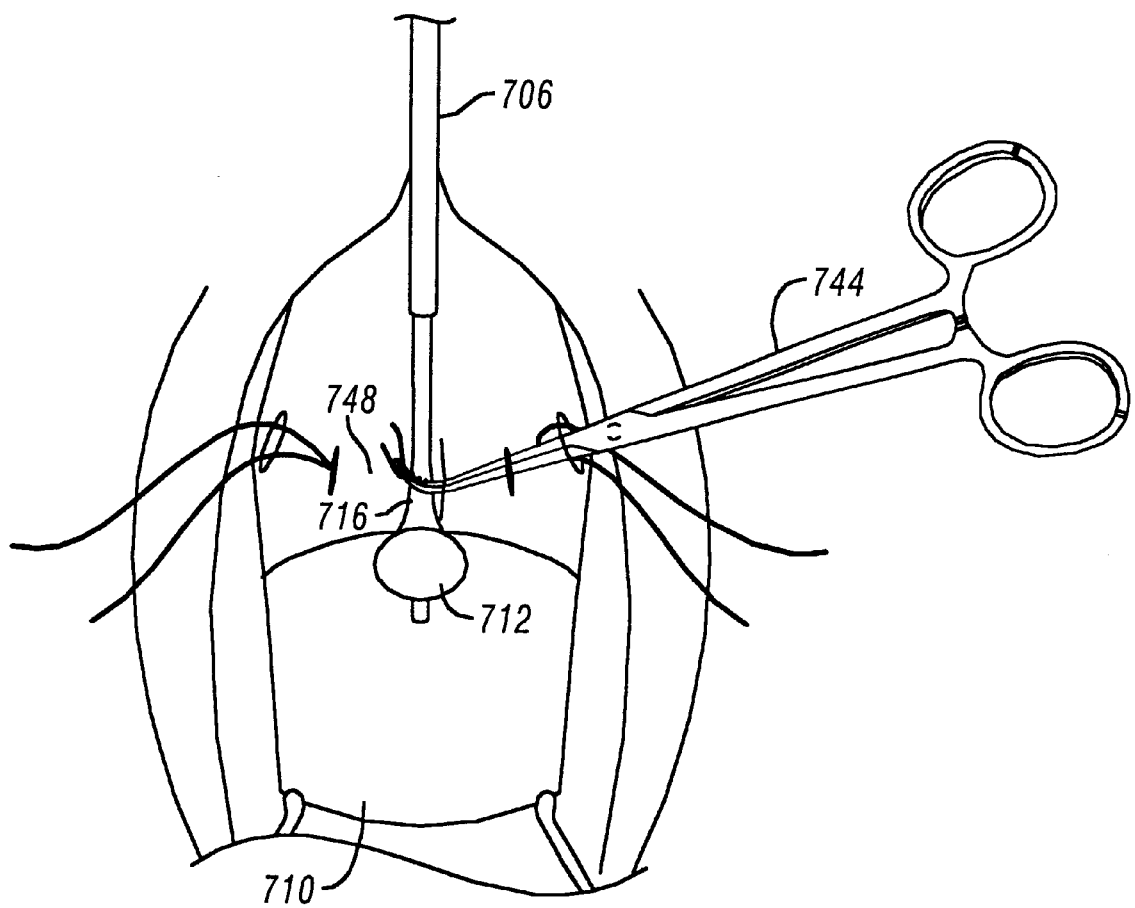
FIG. 32 is a cross sectional view of a patient's vagina showing a subsequent step in the submucosal tunnel technique of the sling procedures of the present invention, in which a right angle dissector is passed submucosally from each vaginal mucosal opening to the midline incision.

A right angle dissector 744 is then passed submucosally from each vaginal mucosal opening to the midline incision 740 to create a submucosal tunnel 748 just below the bladder neck 716, as shown in FIG. 32.

Figure 33:
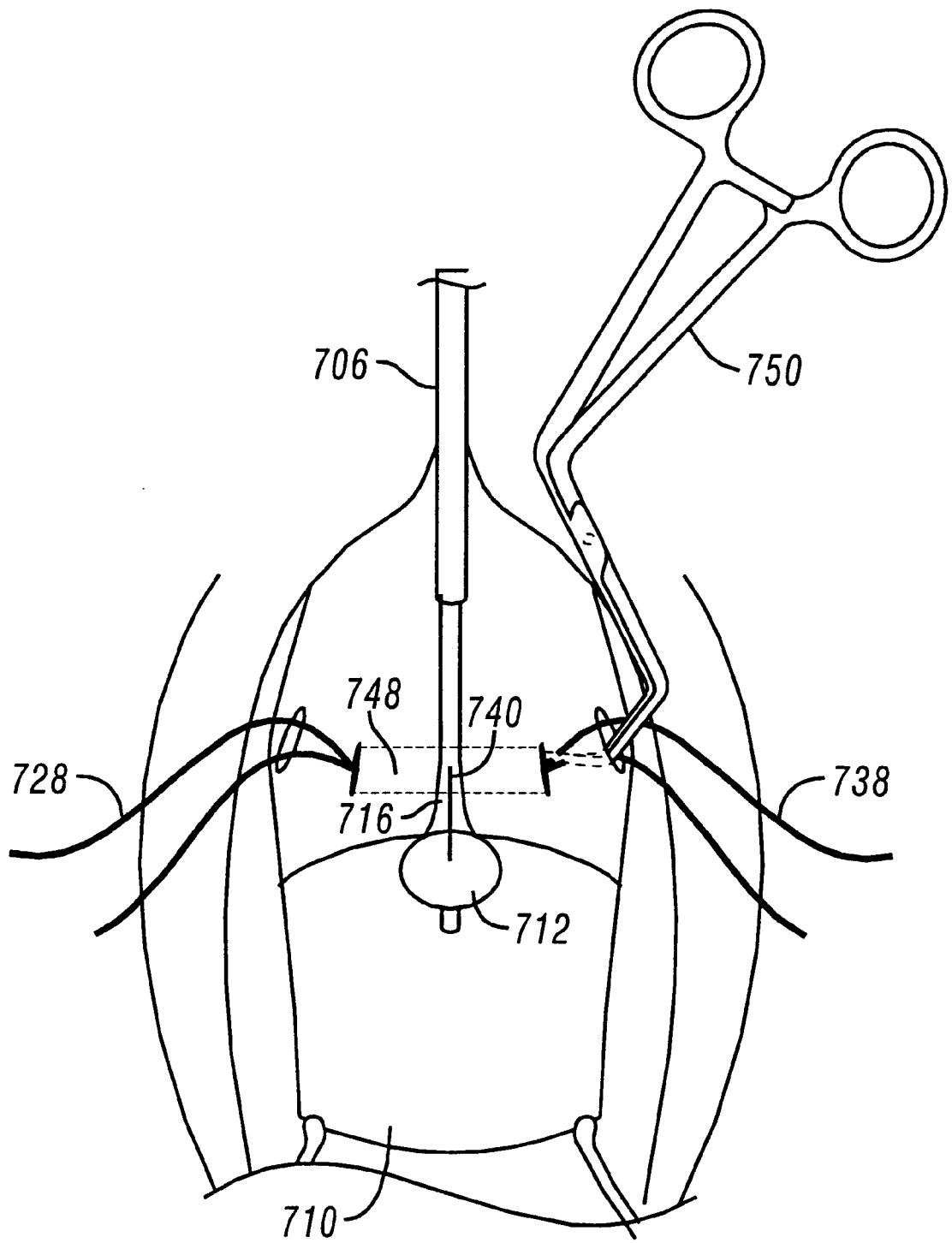
FIG. 33 is a cross sectional view of a patient's vagina showing a subsequent step in the submucosal tunnel technique of the sling procedures of the present invention, in which the tunnels created by the anchor's sutures are dilated using a medical dilator.

The tunnels created by the anchor's sutures are then dilated. Dilation is performed by threading one pair of sutures through the tip of a dilator 750. The dilator 750 is inserted into the vagina and, while pulling on the sutures, it is advanced and pushed up along the sutures, perpendicular to the pubic bone surface, as shown in FIG. 33. Once the dilator 750 touches the bone cortex, the dilator is then opened approximately 5 mm and pulled back, and out of the patient, in the open position. This procedure is then repeated for the contralateral pair of sutures.

Figure 34:
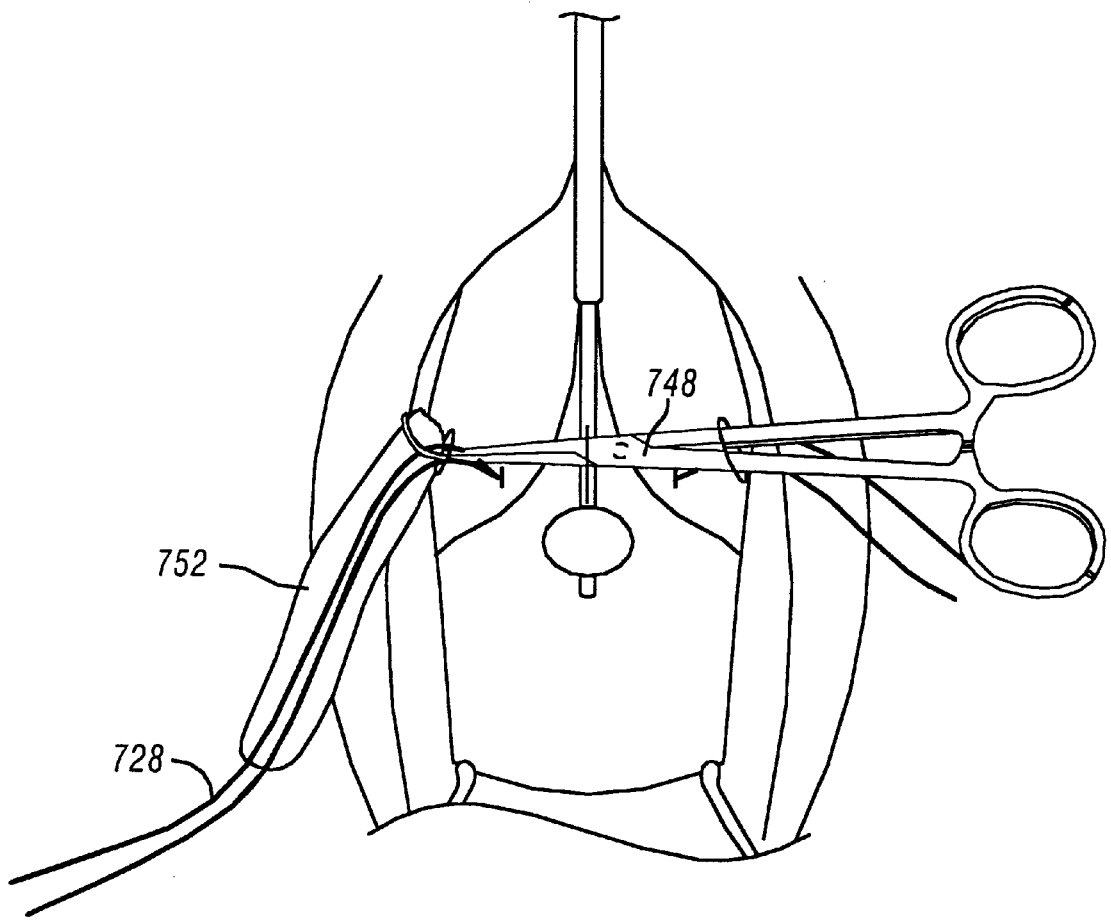
FIG. 34 is a cross sectional view of a patient showing a subsequent step in the submucosal tunnel technique of the sling procedures of the present invention, in which two sutures on one side of the midline incision are threaded through two holes in one side of the sling (one suture per hole), and in which the sling material is passed through the submucosal tunnel from one side to the other.

Once the tunnels created by the sutures have been dilated, the sling is introduced into the vagina. As shown in FIG. 34, the two sutures 728 on one side are threaded through the two holes in one side of the sling 752. The sling material 752 is then passed through the submucosal tunnel from one side to the other.

Figure 35:
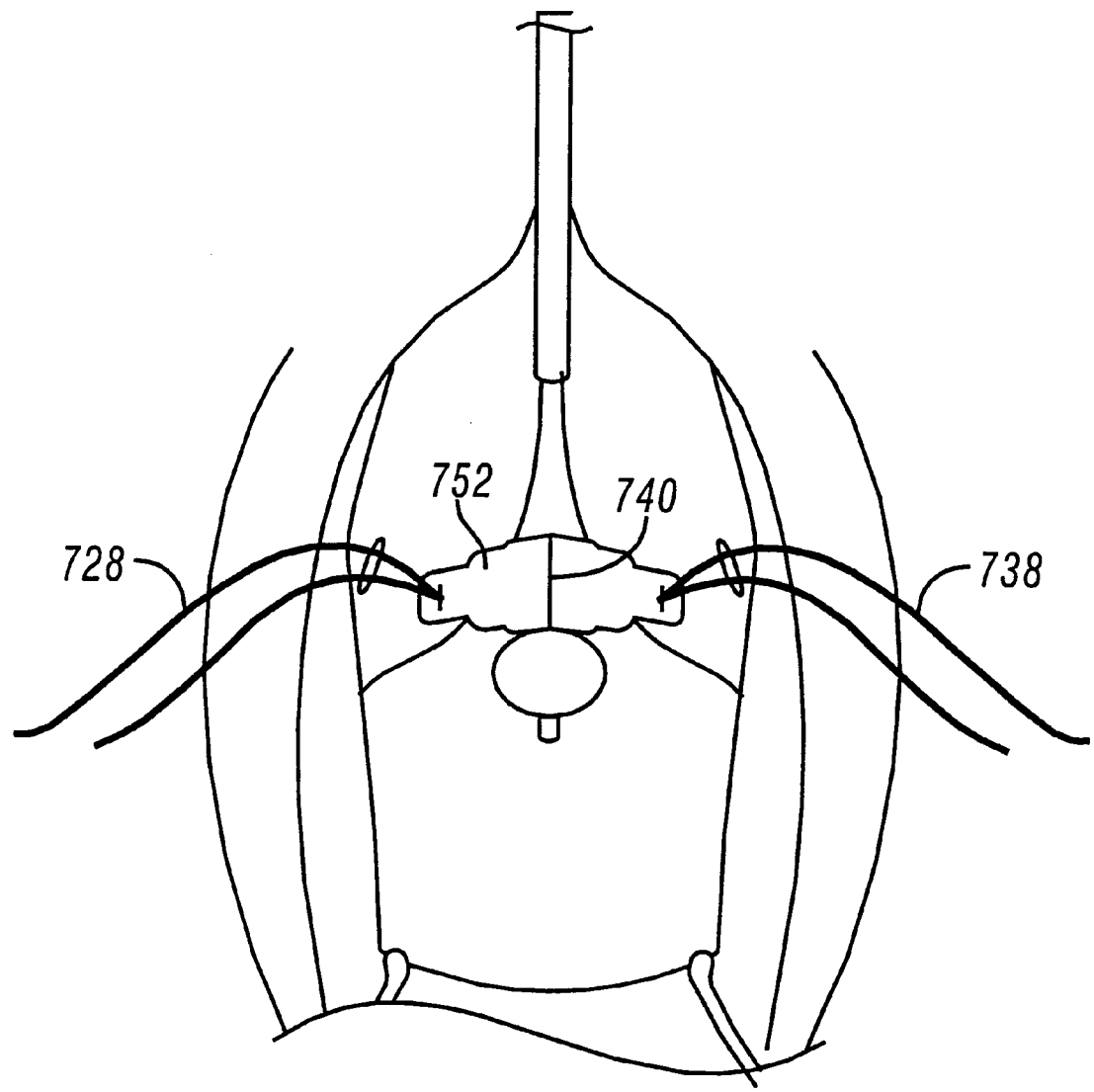
FIG. 35 is a cross sectional view of a patient's vagina showing a subsequent step in the submucosal tunnel technique of the sling procedures of the present invention, in which the sling is loosely tied to the pubic bone.

As shown in FIG. 35, when the sling 752 has been advanced across the tunnel, two sutures on one side are tied towards the pubic bone to affix the sling to the pubic bone surface. On the other side, only a single knot is tied to enable fine tuning of the sling tension, if required.

Figure 36:
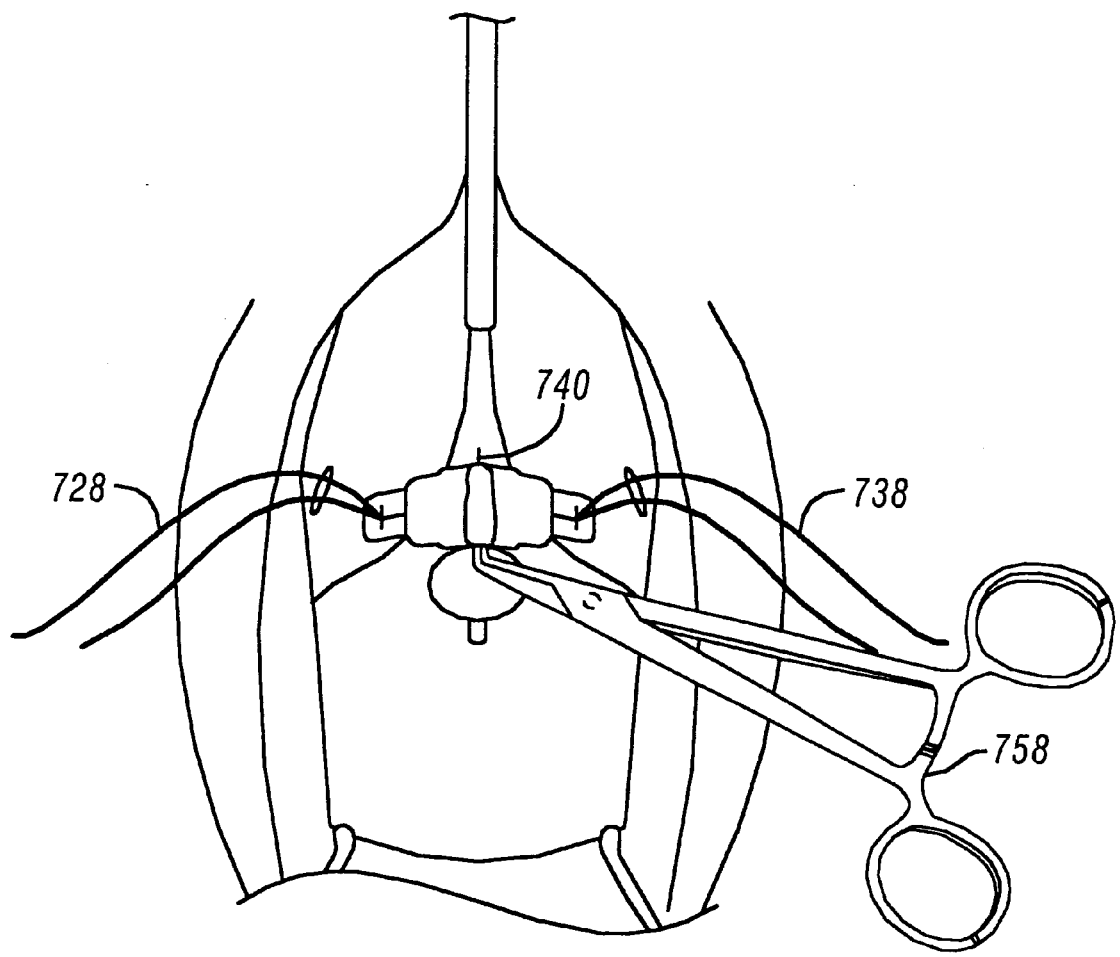
FIG. 36 is a cross sectional view of a patient's vagina showing a subsequent step in the submucosal tunnel technique of the sling procedures of the present invention, in which the sling's tension is tested, preferably using a right angle dissector, and adjusted, if necessary. Once the desired tension is present, sling is tightly secured.
Figure 37:
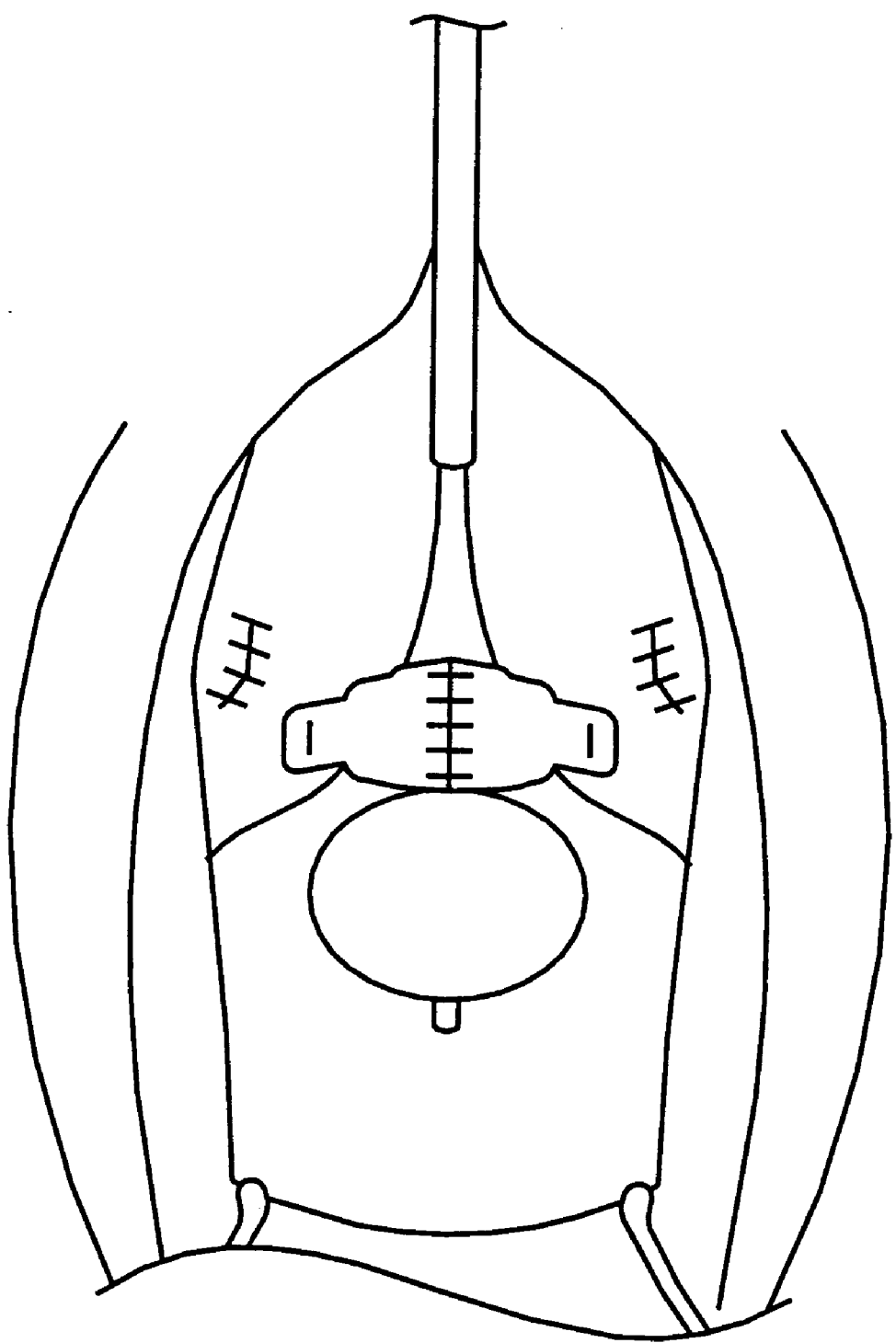
FIG. 37 is a cross sectional view of a patient's vagina showing a subsequent step in the submucosal tunnel technique of the sling procedures of the present invention, in which the vaginal mucosal incisions are closed with sutures.

To check the sling's tension, a right angle clamp 758 is inserted through the midline incision 740 above the sling material 752 and used to pull the sling material downwards gently, as shown in FIG. 36. The sling 752 should be loose enough to permit approximately 0.5 cm of sling movement. If the sling is too tight or too loose, the sling tension is adjusted (by adjusting the tension on the side with the single knot), and then, once sufficient tension has been achieved, that side of the sling is secured. The vaginal mucosal incisions are then closed with absorbable sutures as shown in FIG. 37.

A suprapubic or urethral catheterization is then performed. The draining catheter should remain until complete bladder emptying is achieved by normal urination, normally between 1 to 2 days. Prophylactic antibiotics should be administered perioperatively for approximately 5 days after the procedure, and physical strain and lifting by the patient should be avoided for 2–3 months. In addition, it is recommended that the lot numbers of the screws used in the procedure should be recorded on the patient's chart. Upon completion of the procedure, the inserter, if of a disposable nature (not reusable) can be discarded.

Anterior Wall Dissection Technique

In an alternate embodiment of the sling procedure of the present invention, an anterior wall dissection technique is provided. In accordance with this embodiment, the initial steps described above with respect to the submucosal tunnel technique are performed, from the antibiotic treatment through the insertion of the second screw on the contralateral side and the performance of a cystoscopy to verify bladder and urethral integrity, as disclosed above, and shown in FIGS. 27–30.

Figure 38:
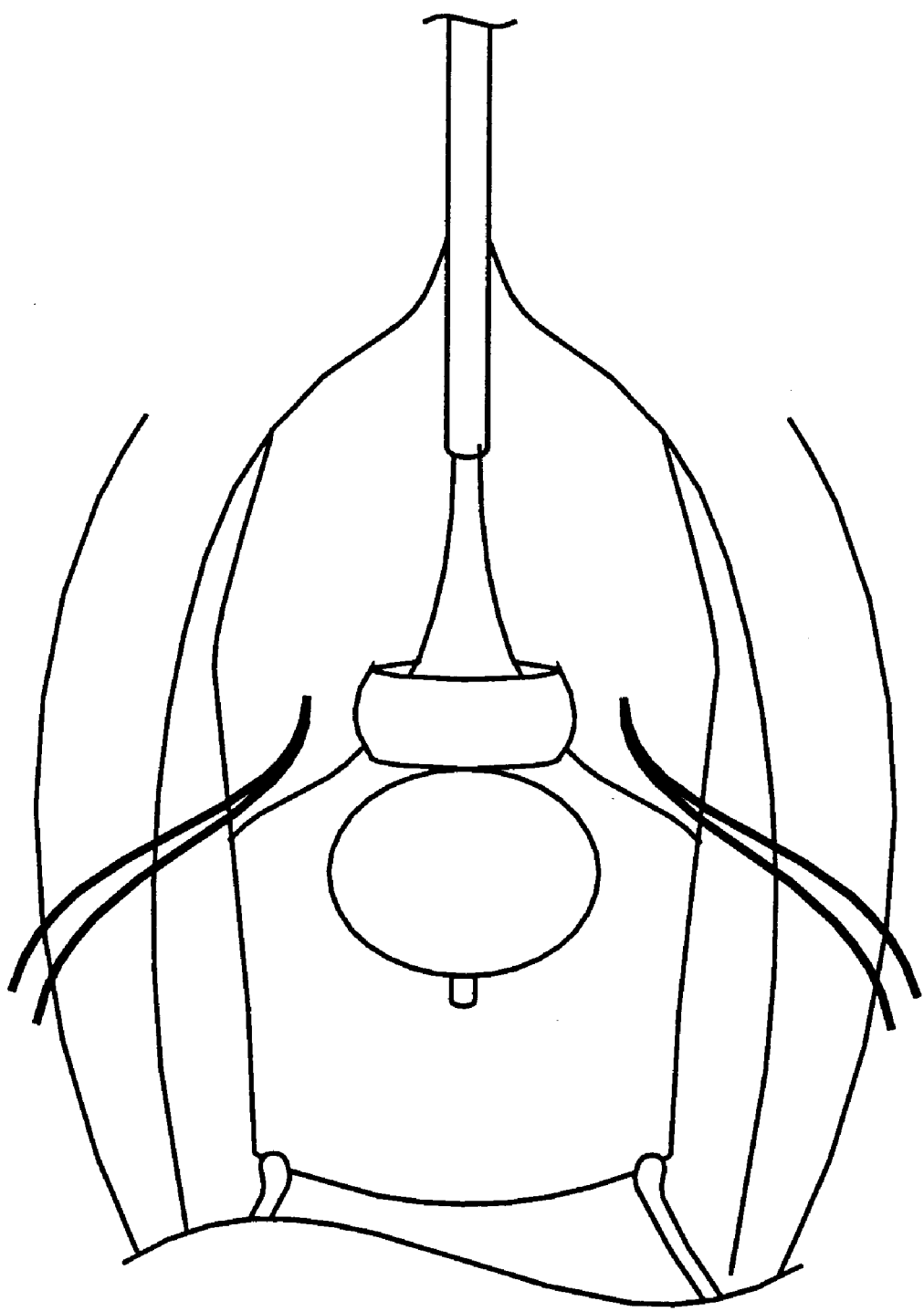
FIG. 38 is a cross sectional view of a patient's vagina showing a first step in the anterior wall dissection technique of the sling procedures of the present invention, in which a U-shaped incision is made. The step of FIG. 38 is performed after conducting the initial steps shown in FIGS. 27–29, the insertion of a second screw as in FIG. 30, and after performing a cystoscopy to verify bladder and urethral integrity. Once these steps are performed, a U-shaped incision is made in the vaginal mucosa, as shown in the figure, with the flap dissected in the anterior vaginal mucosa, exposing the periurethral tissue. Any other technique of vaginal wall dissection can also be performed.

Following the cystoscopy, a U or other incision is made in the vaginal mucosa. The flap is dissected in the anterior vaginal mucosa, exposing the periurethral tissue as shown in FIG. 38.

Figure 39:
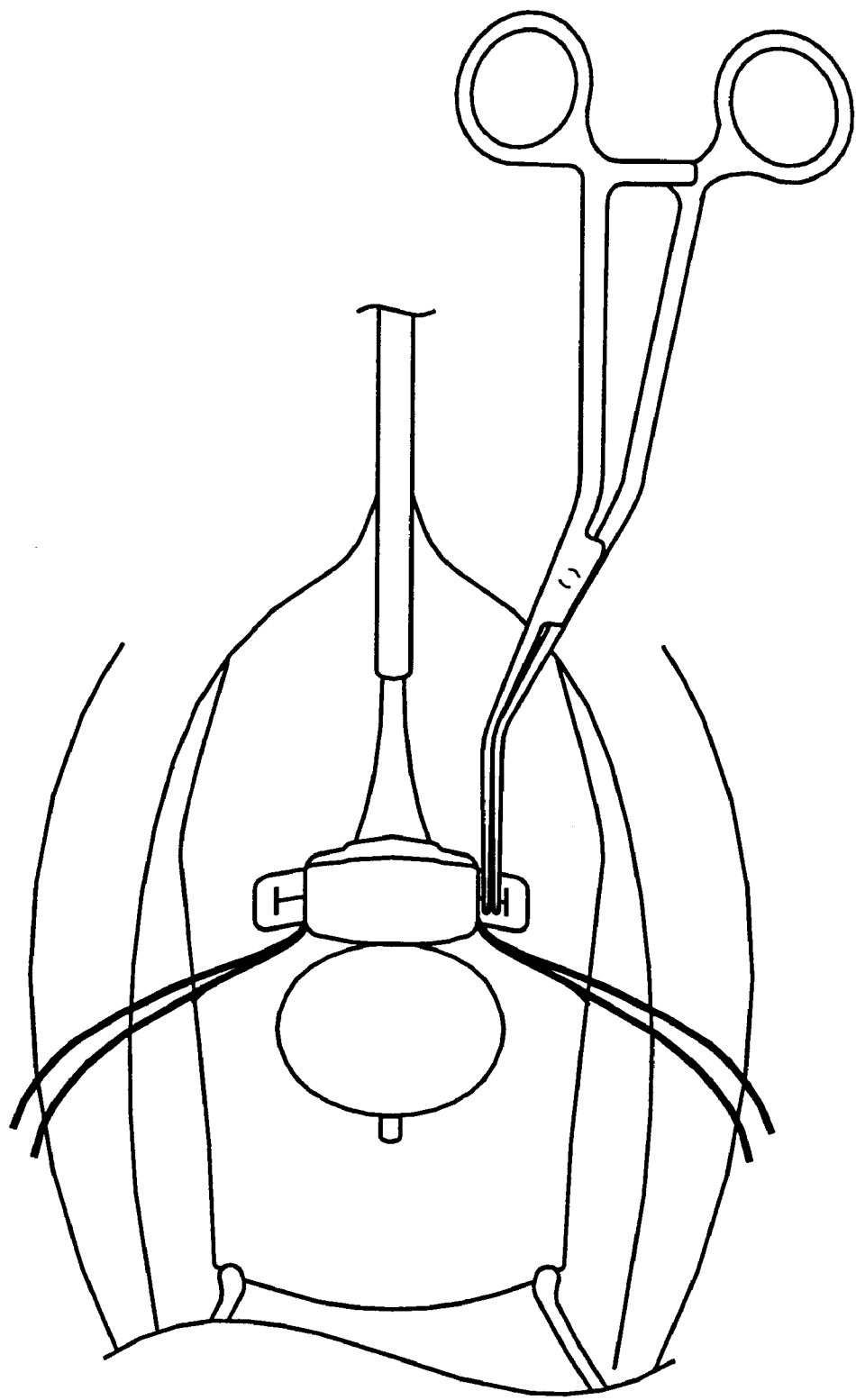
FIG. 39 is a cross sectional view of a patient's vagina showing a subsequent step in the anterior wall dissection technique of the sling procedures of the present invention, in which the tunnels created by the anchor's sutures are dilated.

The tunnels created by the anchor's sutures are then dilated, as shown in FIG. 39. This is performed by threading one pair of sutures through the tip of a dilator. The suture is then held, under tension, and the dilator is pushed up along the sutures, perpendicular to the pubic bone surface. Once the dilator touches the bone cortex, the dilator is opened approximately 5 mm and pulled back, and out of the patient, in the open position. This procedure is then repeated for the contralateral pair of sutures.

Figure 40:
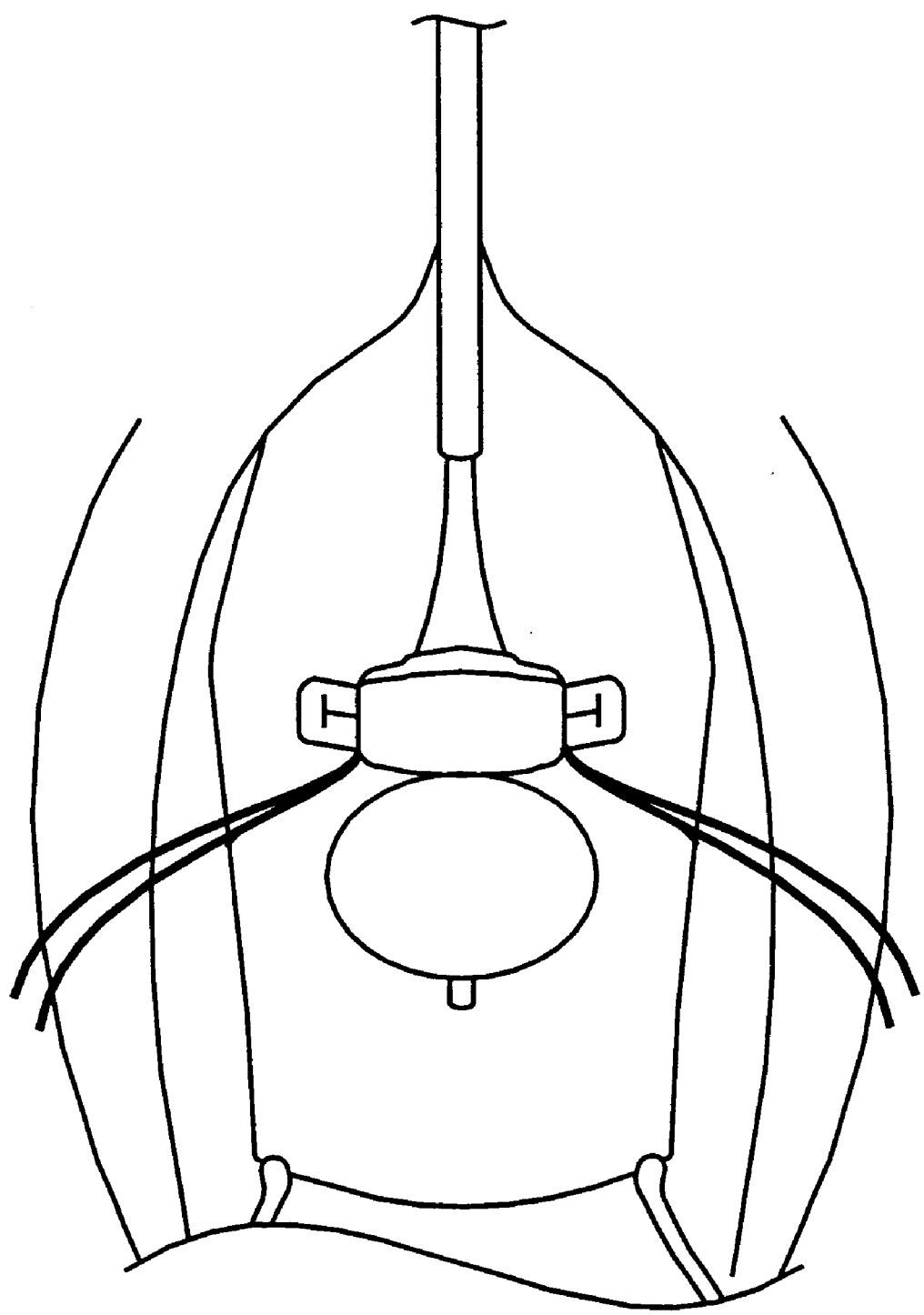
FIG. 40 is a cross sectional view of a patient's vagina showing a subsequent step in the anterior wall dissection technique of the sling procedures of the present invention, in which the sling is placed below the bladder neck, on the exposed tissue, and the sling is tied to the pubic bone surface by threading two sutures, on each side of the sling, through the two holes on that side.
Figure 41:
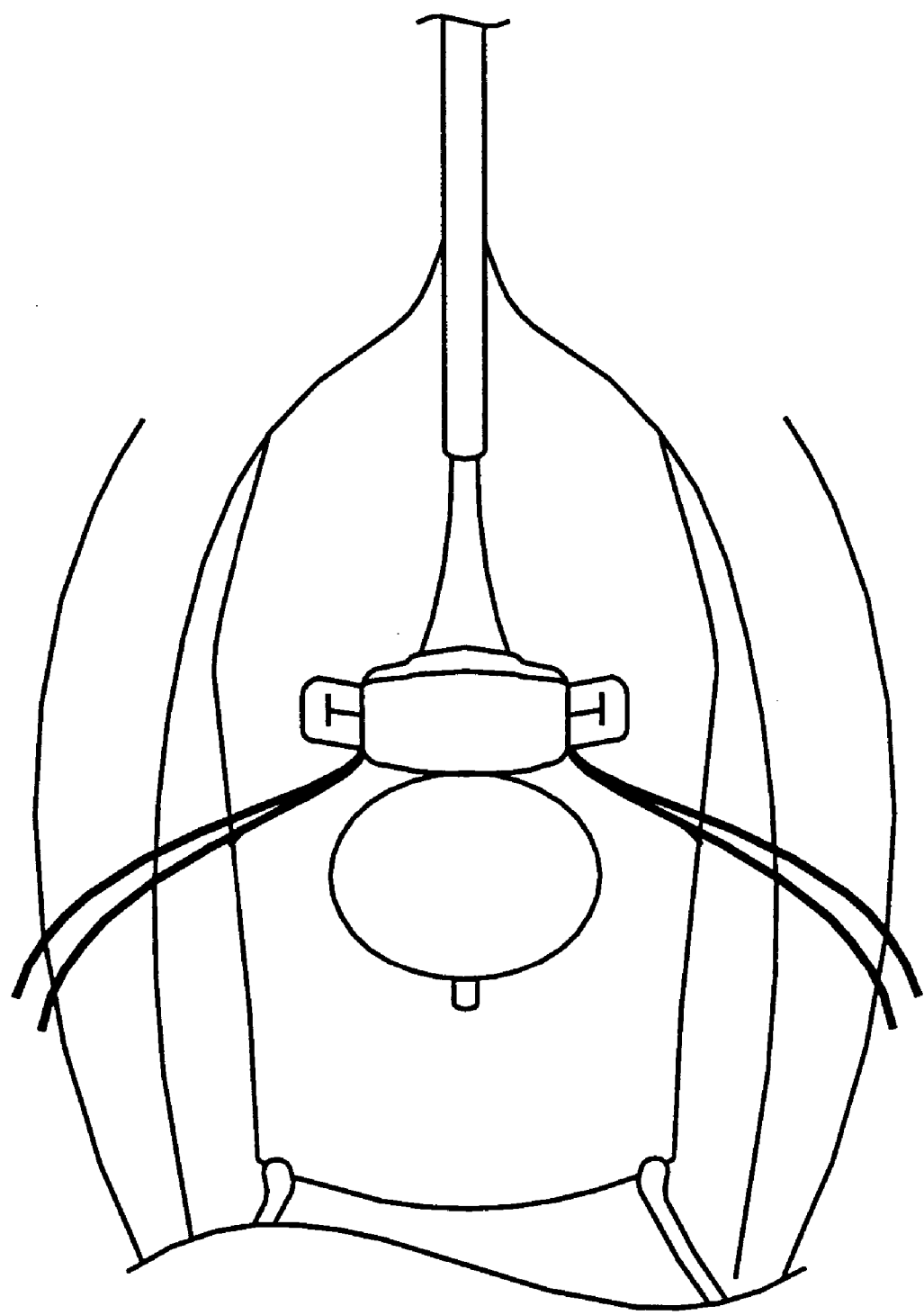
FIG. 41 is a cross sectional view of a patient's vagina showing a subsequent step in the anterior wall dissection technique of the sling procedures of the present invention, in which two sutures are tied on one side of the sling to affix the sling to the pubic bone surface, and in which, only one knot is tied on the other side, to enable fine tuning of the sling tension.

The sling is then placed below the bladder neck, on the exposed tissue. On each side of the sling, two sutures are threaded through the two holes in the sling on that side, a suture through each hole, as shown in FIG. 40. On one side, two sutures are tied toward the pubic bone to affix the sling to the pubic bone surface. On the other side, only one knot is tied so as to enable fine tuning of the sling tension if required, as with the submucosal tunnel technique, and as shown in FIG. 41.

Figure 42:
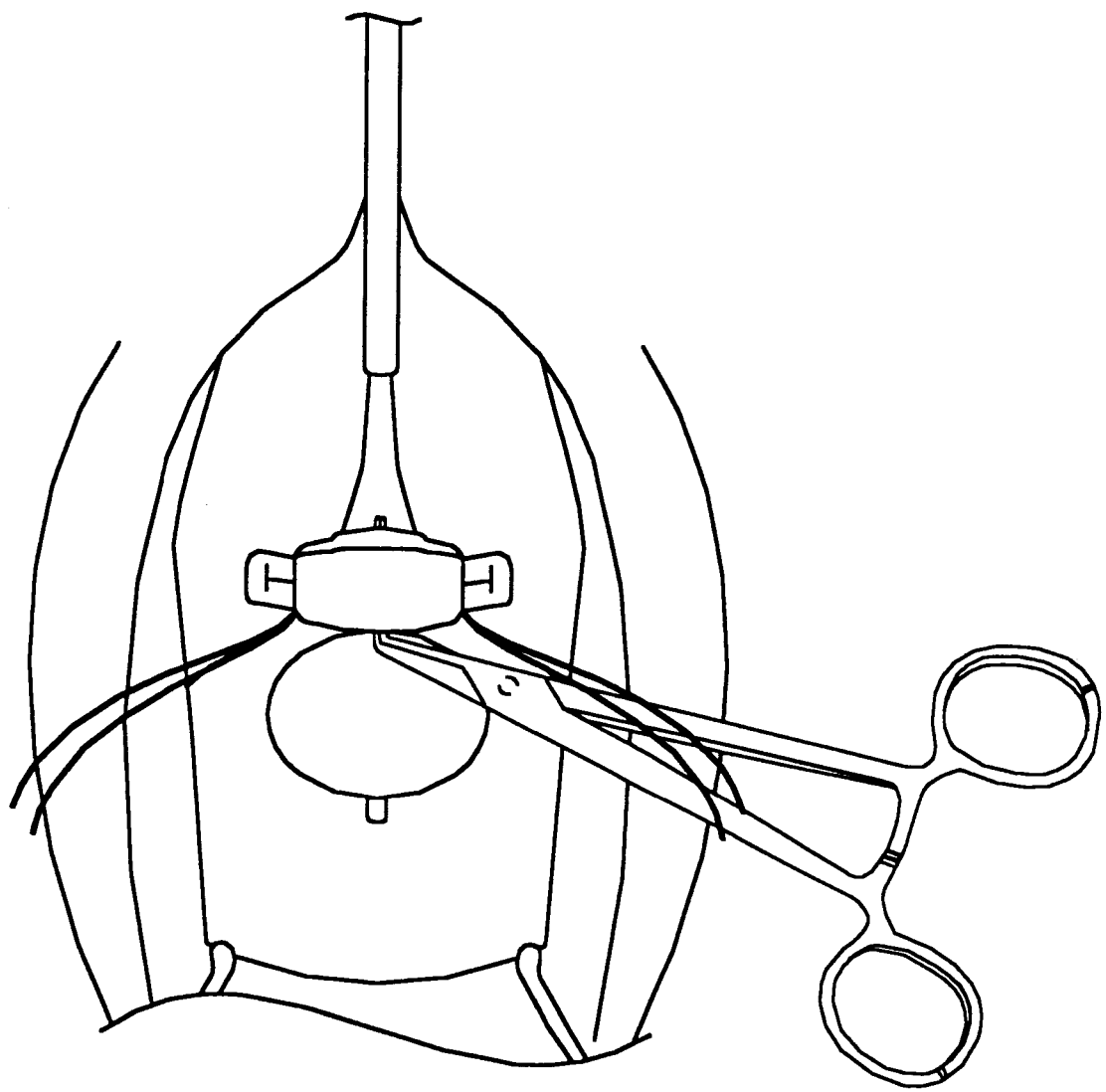
FIG. 42 is a cross sectional view of a patient's vagina showing a subsequent step in the anterior wall dissection technique of the sling procedures of the present invention, in which the sling's tension is checked, preferably using a right angle dissector. Once the desired tension is present, sling is tightly secured.
Figure 43:
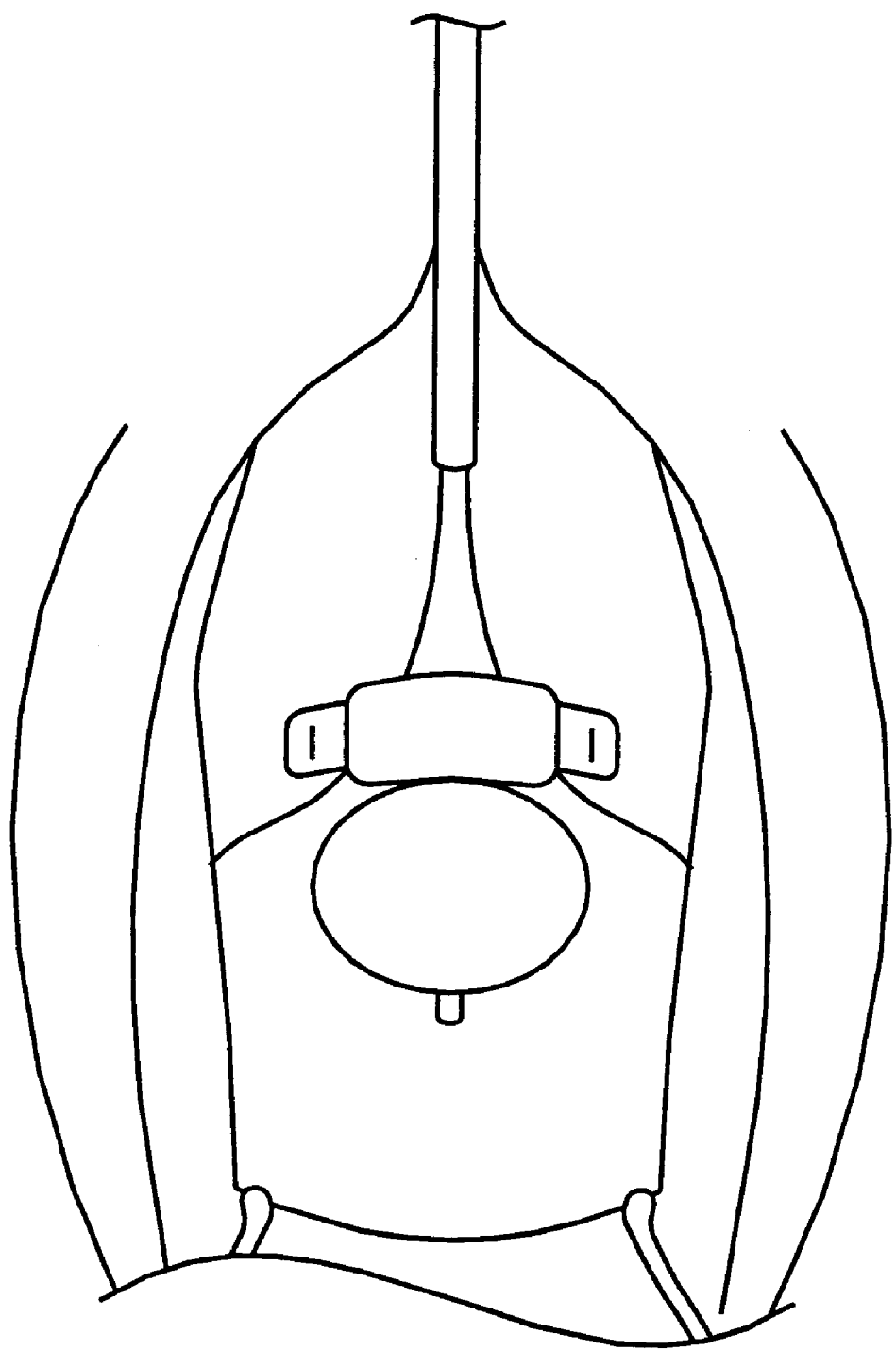
FIG. 43 is a cross sectional view of a patient's vagina showing a subsequent step in the anterior wall dissection technique of the sling procedures of the present invention, in which the vaginal muscosal flap is closed with absorbable sutures.

To check the sling's tension, a right angle clamp is placed above the sling material and pulled downwards gently, as shown in FIG. 42. The sling should be loose enough to permit up to 0.5 cm of sling movement. The vaginal mucosal flap is then closed with absorbable sutures, as shown in FIG. 43.

A suprapubic or urethral catheterization is then performed. The draining catheter should remain until complete bladder emptying is achieved by normal urination, normally between 1 to at 2 days. Prophylactic antibiotics should be administered perioperatively for approximately 5 days after the procedure, and physical strain and lifting by the patient should be avoided for 2–3 months. In addition, it is recommended that the lot numbers of the screws used in the procedure should be recorded on the patient's chart. Upon completion of the procedure, the inserter can be discarded.

Non-Screw Bone Anchor Techniques

In alternate embodiments of the invention, the Submucosal Tunnel Technique and the Anterior Wall Dissection can be performed with a non-screw bone anchor. In the preferred embodiment, such insertions are performed using the In-Tac™ Bone Anchor System, available from Influence, Inc. of San Francisco, Calif.

In these embodiments, the procedure is also conducted using a pervaginal insertion of an anchor into the patient. After a perioperative antibiotic treatment, the patient is placed under spinal, general or local anesthesia and in the lithotomy position, and the surgical area and the vagina are cleaned and disinfected.

The anchor inserter is then loaded with an anchor. Initially, the loading key is placed into its key hole on the inserter and the key is turned clockwise approximately one half turn until the loading key will not turn further. The first anchor is then placed within the anchor inserter.

A Foley catheter is then inserted inside the bladder, and the balloon is inflated with approximately 10–20 cc of water, as previously described. The catheter is then gently pulled to locate the balloon just above the bladder neck, as shown in FIG. 27.

When the balloon 712 has been positioned, the catheter 706 is then located, within the urethra, between the physician's index and second fingers so that the finger tips are touching the balloon at the bladder neck. The physician then, by pushing his or her fingers upward and forward, presses the anterior vaginal wall against the posterior of the pubic bone 718, as shown in FIG. 28.

Figure 44:
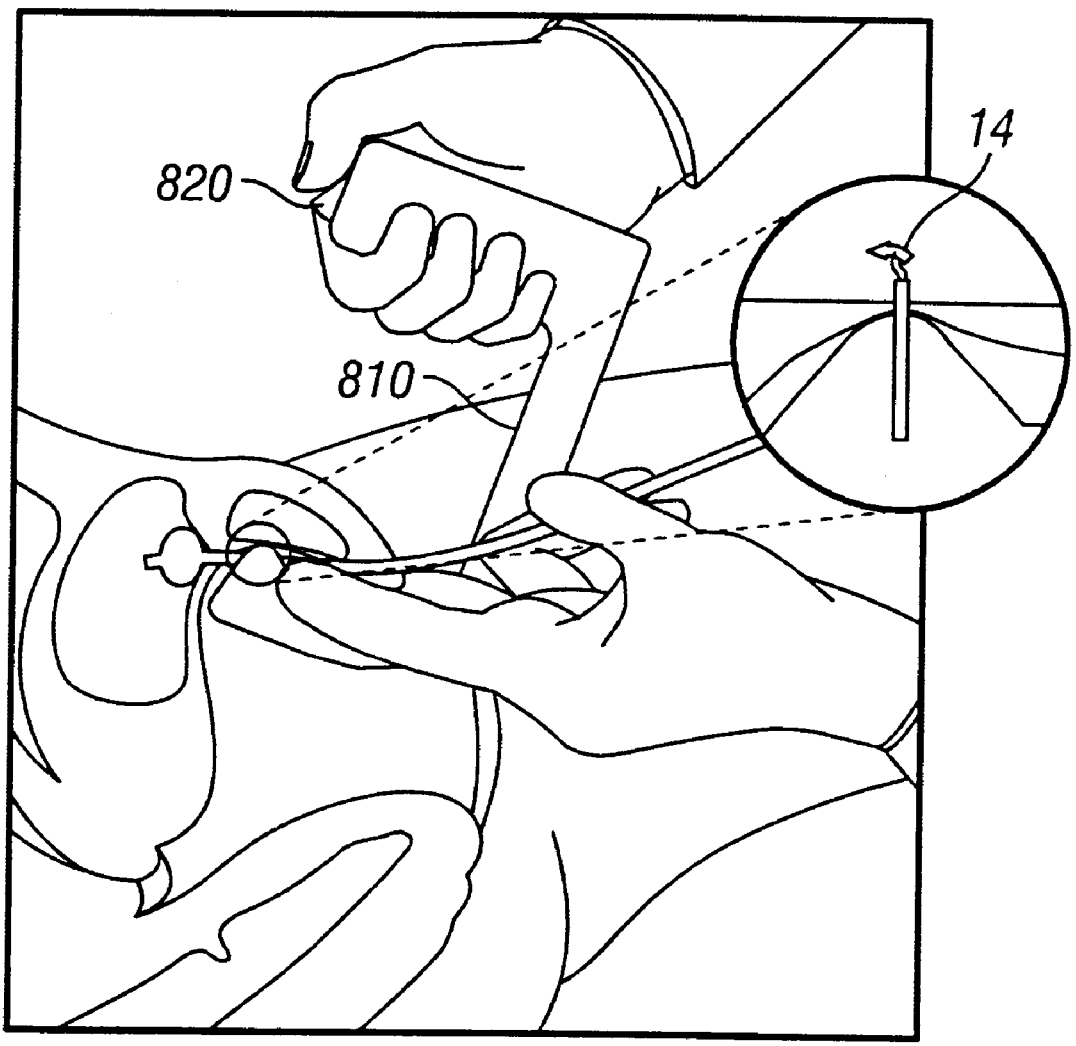
FIG. 44 is a cross sectional view of a patient's vagina showing the use of a non-linear anchor inserter, for insertion of a non-screw anchor into the public bone, in accordance with a sling procedure of the present invention, as disclosed herein.

As shown in FIG. 44, while still feeling the catheter within the urethra, the bone anchor inserter is inserted into the vagina, below the bladder neck, lateral to the symphysis pubis, about 2 cm. to the side of the urethra, and pulled upward until the anchor housing is pressing the anterior vaginal wall against the pubic bone. The anchor shield will then retract or collapse and the tip of the bone anchor should be exposed to enable it to penetrate the vaginal wall and enter the cortex of the pubic bone, as also shown in FIG. 44.

The safety lock of the inserter is then released, and the physician pulls upwards on the handle of the inserter until an anchor is deployed. Preferably, the safety lock will not allow anchor deployment unless sufficient pressure is applied to the inserter handle. The physician can then continue with either the Submucosal Tunnel Technique or the Anterior Wall Dissection technique, as described above.

Figure 45A:
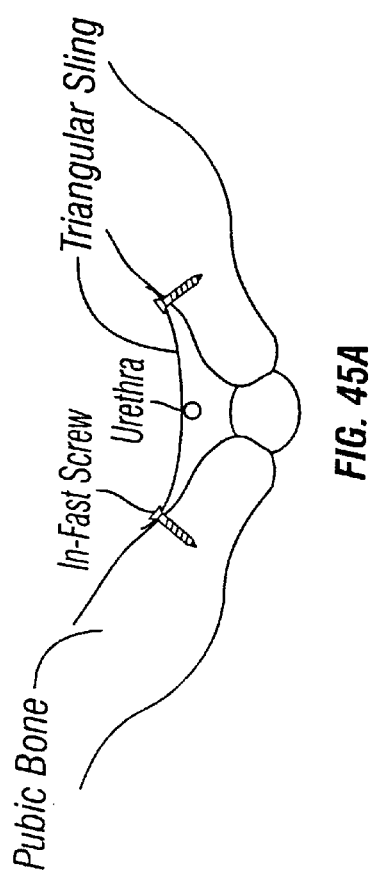
FIG. 45(a) is a cross sectional view showing a sling attached upward and forward to the mid-pubic bone, just below the Cooper's ligament.
Figure 45B:
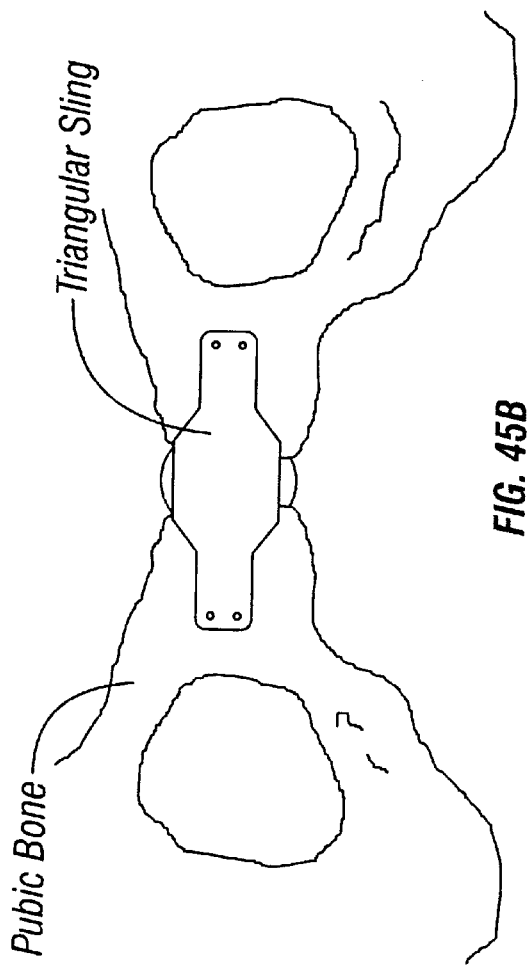
FIG. 45(b) is a further view of the sling of FIG. 45(a) shown as a view of the posterior pubic bone.

A further embodiment of the invention in which the sling material is pervaginally suspended from the pubic bone is shown in FIGS. 45(a) and (b). FIG. 45(a) shows a sling material wherein the sling is attached upward and forward to the mid-pubic bone, just below the Coooper's ligament. A triangle is formed by the sling material and the natural "V" of the pubic bone, providing a "free space" for the urethra which may reduce the tendency for overcorrection. FIG. 45(b) illustrates the sling of FIG. 45(a), taken as a view of the posterior pubic bone. In these embodiments, the sling material is positioned as a hammock below a portion of the female anatomy (i.e. the bladder neck and/or the urethra), the sling being suspended to the posterior surface of the pubic bone by a pervaginal technique, and with the bone anchors likewise being inserted pervaginally. In the preferred embodiment of the invention of FIG. 45, the sling is directly attached to the pubic bone without the use of intervening sutures, preferably by inserting a bone anchor through the sling material to directly attach the sling to the pubic bone.

Figure 46:
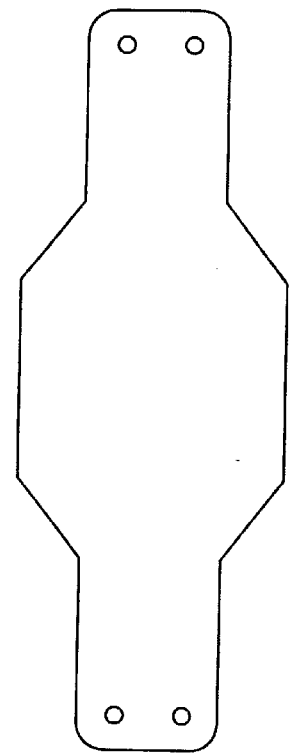
FIG. 46 is a plain view of a preferred sling design, in accordance with the present invention.

In accordance with the inventions of the present application, one prefe rred sling design is shown in FIG. 46. This sling is preferably a biocompatible texturized fabric impregnated with an absorbable gelatin. It is preferred that a soft pliable material with a matrix that facilitates tissue ingrowth be used. The material can be formed with a warp knitting process. Gelatin impregnation is preferably crosslinked to a set level to control the resorption rate and reduce the potential for inflammation. The sling is also preferably prepunctured to facilitate the threading of suture or insert ion of a bone anchor therethrough. In one preferred embodiment, the sling is approximately 5.5 cm in length and approximately 2 cm in width at its widest portion.

Having described this invention with regard to specific embodiments, it is to be understood that the description is not meant as a limitation since further variations or modifications may be apparent or may suggest themselves to those skilled in the art. It is intended that the present application cover such variations and modifications as fall within the scope of the appended claims.

What is claimed is:

1. A method of treating a female patient for urinary stress incontinence, comprising:

per vaginally inserting a bone anchor to enter the posterior wall of the pubic bone, said bone anchor comprising suture thread secured thereto; and, using said suture thread and a sling, made of a biocompatible texturized fabric impregnated with an absorbable gelatinous substance, to treat the incontinence.

2. The method as claimed in claim 1, wherein said bone anchor is a staple type bone anchor, and comprises suture thread attached thereto; and further comprising using said suture thread and a sling to adjust the anatomy of the patient.

3. A method as claimed in claim 2, wherein said suture thread and said sling are used to adjust the position of the bladder neck of the patient.

4. A method as claimed in claim 2, wherein said suture thread and said sling are used to adjust the position of the urethra of the patient.

5. A method of treating a female patient for urinary stress incontinence, comprising:

per vaginally inserting a bone anchor;

employing a pulling force on said bone anchor perpendicularly against the pubic bone of the patient to enter the posterior wall of the pubic bone by use of a bone anchor inserter; and using suture thread and a sling made of a biocompatible texturized fabric impregnated with an absorbable gelatinous substance to adjust the anatomic position of the bladder neck and the urethra of the patient.

6. A method as claimed in claim 5, wherein said anchor comprises a bone screw, said bone screw comprising suture thread secured thereto.

7. A method as claimed in claim 5, wherein said anchor comprises a staple type bone anchor, said bone anchor comprising suture thread secured thereto.

8. A method as claimed in claim 5, wherein said bone anchor inserter comprises a nonlinear bone anchor inserter.

9. A method as claimed in claim 8, wherein said nonlinear bone anchor inserter comprises a retractable shield.

10. A method as claimed in claim 5, further comprising creating a submucosal tunnel below the bladder neck.

11. A method as claimed in claim 10, wherein said submucosal tunnel is created using a dilator.

12. A method as claimed in claim 10, further comprising passing said sling through said submucosal tunnel.

13. A method as claimed in claim 12, further comprising tying said sling to the pubic bone.

14. A method as claimed in claim 13, further comprising checking and adjusting, if necessary, the tension of said sling.

15. A method as claimed in claim 14, wherein said tension of said sling is checked using a right angle dissector.

16. A method as claimed in claim 5, further comprising creating a U shaped incision in the vaginal mucosa.

17. A method as claimed in claim 5, wherein said sutures pass though tissue to create a tunnel, and further comprising the step of dilating said tunnel.

18. A method as claimed in claim 17, wherein said tunnel is dilated using a dilator.

19. A method as claimed in claim 18, further comprising passing said sling through said tunnel.

20. A method as claimed in claim 19, further comprising tying said sling to the pubic bone.

21. A method as claimed in claim 20, further comprising checking and adjusting, if necessary, the tension of said sling.

22. A method as claimed in claim 21, wherein said tension of said sling is checked using a right angle dissector.

23. A method of treatment for female urinary stress incontinence comprising:

providing a sling material and staple type bone anchors; and, positioning said sling material below a portion of at least one of a bladder neck and urethra, said sling material being positioned as a hammock and being pervaginally suspended to the posterior surface of the pubic bone using said staple type bone anchors, said staple type bone anchors being inserted pervaginally.

* * * * *

UNITED STATES PATENT AND TRADEMARK OFFICE
CERTIFICATE OF CORRECTION

PATENT NO. : 6,334,446 B1  Page 1 of 1
DATED : January 1, 2002
INVENTOR(S) : Beyer It is certified that error appears in the above-identified patent and that said Letters Patent is hereby corrected as shown below:

<u>Column 20,</u>
Lines 27-34, claim 1, should read as follows:
1. A method of treating a female patient for urinary stress incontinence, comprising:
per vaginally inserting a bone anchor to enter the posterior wall of the pubic bone by use of a non-linear bone anchor inserter.

Signed and Sealed this

Twenty-eighth Day of May, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,334,446 B1
DATED         : January 1, 2002
INVENTOR(S)   : Beyar It is certified that error appears in the above-identified patent and that said Letters Patent is hereby corrected as shown below:

<u>Title page,</u>
Item [73], should read as:
-- [73] Assignee: American Medical Systems International, Inc., Minnetonka, MN (US) --.

Signed and Sealed this

Second Day of September, 2003

JAMES E. ROGAN
*Director of the United States Patent and Trademark Office*